(12) United States Patent
Ando

(10) Patent No.: US 11,009,723 B2
(45) Date of Patent: May 18, 2021

(54) OPHTHALMIC DIFFRACTIVE MULTI-FOCAL LENS AND METHOD FOR MANUFACTURING OPHTHALMIC DIFFRACTIVE MULTI-FOCAL LENS

(71) Applicant: MENICON CO., LTD., Nagoya (JP)

(72) Inventor: Ichiro Ando, Kasugai (JP)

(73) Assignee: MENICON CO., LTD., Nagoya (JP)

(*) Notice: Subject to any disclaimer, the term of this patent is extended or adjusted under 35 U.S.C. 154(b) by 351 days.

(21) Appl. No.: 16/074,617

(22) PCT Filed: Feb. 9, 2016

(86) PCT No.: PCT/JP2016/053874
§ 371 (c)(1),
(2) Date: Aug. 1, 2018

(87) PCT Pub. No.: WO2017/138099
PCT Pub. Date: Aug. 17, 2017

(65) Prior Publication Data
US 2019/0041664 A1    Feb. 7, 2019

(51) Int. Cl.
*G02C 7/04*    (2006.01)
*G02B 5/18*    (2006.01)
(Continued)

(52) U.S. Cl.
CPC ............ *G02C 7/044* (2013.01); *A61F 2/1618* (2013.01); *A61F 2/1654* (2013.01);
(Continued)

(58) Field of Classification Search
CPC .. G02C 7/044; G02C 7/02; G02C 7/04; A61F 2/1618; A61F 2/1654; A61F 2/1656; A61F 2240/001; G02B 5/18
(Continued)

(56) References Cited

U.S. PATENT DOCUMENTS 6,829,093 B1    12/2004  Nakai
9,304,329 B2 *   4/2016  Zhao ................... A61F 2/16
(Continued)

FOREIGN PATENT DOCUMENTS

EP    3 179 294 A1    6/2017
EP    3 358 395 A1    8/2018
(Continued)

OTHER PUBLICATIONS

Jan. 30, 2019 Office Action issued in Japanese Patent Application No. 2017-566451.
(Continued)

*Primary Examiner* — Marin Pichler
*Assistant Examiner* — Mitchell T Oestreich
(74) *Attorney, Agent, or Firm* — Oliff PLC

(57) ABSTRACT

Provided is an ophthalmic diffractive multi-focal lens with a diffractive structure including a phase profile in which a plurality of blaze shaped zones are set in a concentric circle form, wherein: at least one of the zones serves as an adjustment zone wherein an inclination direction in the phase profile is reversed with respect to that of other zones; and a light intensity level giving a peak or focal point at a position away from three focal points in a light intensity distribution of transmitted light in an optical axis direction is kept low in comparison with a phase profile without the adjustment zone.

11 Claims, 12 Drawing Sheets

(51) Int. Cl.
*G02C 7/02* (2006.01)
*A61F 2/16* (2006.01)
(52) U.S. Cl.
CPC .............. *A61F 2/1656* (2013.01); *G02B 5/18* (2013.01); *G02C 7/02* (2013.01); *G02C 7/04* (2013.01); *A61F 2240/001* (2013.01)
(58) Field of Classification Search
USPC .................................................... 359/159.12
See application file for complete search history.

(56) References Cited

U.S. PATENT DOCUMENTS

| 2011/0270390 | A1 | 11/2011 | Kobayashi et al. |
| 2012/0283825 | A1 | 11/2012 | Houbrechts et al. |
| 2017/0227789 | A1 | 8/2017 | Ando et al. |

FOREIGN PATENT DOCUMENTS

| JP | 2001-042112 A | 2/2001 |
| JP | 2010-158315 A | 7/2010 |
| JP | 2012-517625 A | 8/2012 |
| JP | 2013-517822 A | 5/2013 |
| WO | 2013/118176 A1 | 8/2013 |
| WO | 2013/118499 A1 | 8/2013 |
| WO | 2014/091528 A1 | 6/2014 |
| WO | 2014/189049 A1 | 11/2014 |
| WO | 2016/021075 A1 | 2/2016 |

OTHER PUBLICATIONS

May 29, 2020 Office Action issued in Japanese Patent Application No. 2017-566451.
Aug. 14, 2018 International Preliminary Report on Patentability issued in International Patent Application No. PCT/JP2016/053874.
Oct. 10, 2019 Extended Search Report issued in European Patent Application No. 16889801.3.
Sep. 3, 2019 Office Action issued in Japanese Patent Application No. 2017-566451.
May 17, 2016 International Search Report issued in International Patent Application No. PCT/JP2016/053874.

\* cited by examiner

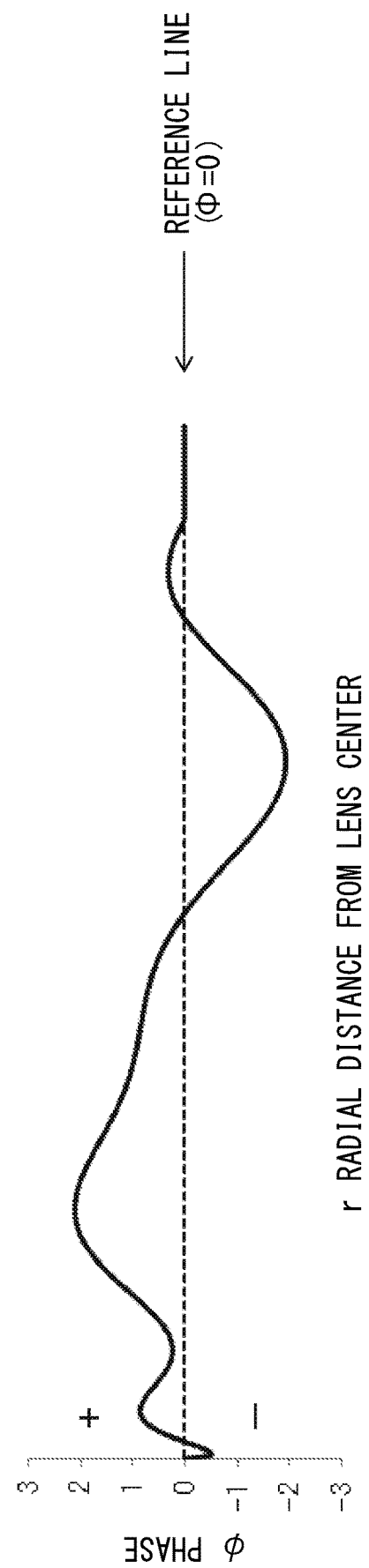

PHASE PROFILE BEFORE ADJUSTMENT

INTENSITY DISTRIBUTION ON OPTICAL AXIS OF PHASE PROFILE BEFORE ADJUSTMENT

PHASE PROFILE OF EXAMPLE 1

INTENSITY DISTRIBUTION ON OPTICAL AXIS OF EXAMPLE 1

PHASE PROFILE OF EXAMPLE 2

INTENSITY DISTRIBUTION ON OPTICAL AXIS OF EXAMPLE 2

PHASE PROFILE OF EXAMPLE 3

INTENSITY DISTRIBUTION ON OPTICAL AXIS OF EXAMPLE 3

PHASE PROFILE OF EXAMPLE 4

INTENSITY DISTRIBUTION ON OPTICAL AXIS OF EXAMPLE 4

PHASE PROFILE OF EXAMPLE 5

INTENSITY DISTRIBUTION ON OPTICAL AXIS OF EXAMPLE 5

PHASE PROFILE OF EXAMPLE 6

INTENSITY DISTRIBUTION ON OPTICAL AXIS OF EXAMPLE 6

PHASE PROFILE OF EXAMPLE 7

INTENSITY DISTRIBUTION ON OPTICAL AXIS OF EXAMPLE 7

OPHTHALMIC DIFFRACTIVE MULTI-FOCAL LENS AND METHOD FOR MANUFACTURING OPHTHALMIC DIFFRACTIVE MULTI-FOCAL LENS

TECHNICAL FIELD

The present invention relates to an ophthalmic lens such as a contact lens, intraocular lens, etc., that is used for the human eye, and exhibits corrective action, etc. on the human eye optical system, and particularly relates to technology of a diffractive multi-focal ophthalmic lens for which a plurality of focal points are set.

BACKGROUND ART

Conventionally, as an optical element for correcting refractive abnormalities in the optical system of the human eye, or as a substitute optical element after removal of an crystalline lens, etc., an ophthalmic lens has been used. As specific ophthalmic lenses, in addition to eyeglasses lenses, there are contact lenses that are overlapped on the cornea, or ophthalmic lenses mounted directly in the human eye, such as an intraocular lens (IOL) used by being inserted intracapsularly in place of the intraocular crystalline lens, or a phakic intraocular lens (ICL) used by being inserted in the anterior chamber of the intraocular crystalline lens, etc., and these are widely used because they provide a wide field of view as well as reduce a sense of discomfort of vision.

However, in recent years, there is an increase in people continuing to use contact lenses when they have reached the age of having presbyopia. For people with presbyopia, their accommodation power decreases, so there is a symptom of having difficulty in focusing on nearby objects. Thus, multi-focal contact lenses which can also focus on nearby objects are needed for presbyopia patients. Also, for patients who have undergone cataract surgery, since the crystalline lens which is in charge of the accommodation function is removed, even if an intraocular lens is inserted as a substitute, the symptom of having difficulty in seeing close up remains. With the intraocular lens as well, it is necessary to have a multi-focal function having a plurality of focal points. In this way, the need for multi-focal ophthalmic lenses to reflect the aging society has increased even further in recent years.

As a method for realizing this multi-focal ophthalmic lens, known examples include a refractive multi-focal ophthalmic lens that forms a plurality of focal points based on the principle of refraction, and a diffractive multi-focal ophthalmic lens that forms a plurality of focal points based on the principle of diffraction. With the latter diffractive ophthalmic lens, provided are a plurality of diffractive structures which are formed in concentric circle form on the optical part of the lens, and a plurality of focal points are given by the mutual interference effect of light waves that pass through the plurality of diffractive structures (zones). Therefore, compared to a refractive lens that gives focal points using the refractive effect of light waves at the refracting surface comprising boundary surfaces with different refractive indexes, with the diffractive type multi-focal ophthalmic lens, there are advantages of being able to set a high lens power while inhibiting an increase in lens thickness, etc.

Generally, a diffractive multi-focal lens has a diffractive structure for which the diffractive zone pitches become gradually narrower toward the periphery from the lens center according to a rule called the Fresnel pitch, and multiple focal points are made by using the 0th order diffracted light and +1st order diffracted light generated from that structure. Normally, the 0th order diffracted light is used as the focal point for far vision, and +1st order diffracted light is used as the focal point for near vision. Using this diffracted light distribution, it is possible to make a bifocal lens having both far and near focal points.

Also, as in Japanese Unexamined Patent Publication No. JP-A-2010-158315 (Patent Document 1) disclosed by the present applicant, or in PCT Japanese Translation Patent Publication No. JP-A-2013-517822 (Patent Document 2), known are items for which the number of focal points are further increased, and as a result, it is possible to set focal points for intermediate vision in addition to those for far vision and for near vision. Moreover, as shown in International Publication No. WO2013/118176 (Patent Document 3) disclosed previously by the present applicant, there is also known a diffractive lens giving a plurality of focal points using a diffractive zone that is not based on the Fresnel pitch.

Meanwhile, with such diffractive multi-focal lens, it is required that, particularly for implementation in an ophthalmic lens, the quality of vision (QOV) be enhanced. For obtaining a good QOV, it is also an effective way to suppress the peak of the light energy other than the focal points required on the optical axis. Specifically, when focusing on the focal point for far vision in the multifocal lens, light from the far distance forms a main peak at the image plane center of the far focal point. Here, due to the fact that the lights intensified each other at other focal point positions, etc. also reach the image plane position of the far focal point, small peak groups exist around the main peak that forms the far focal point in the image plane of the far focal point, which conceivably cause the light energy other than the required focal points.

Therefore, in the multifocal lens, it may be effective for enhancing the QOV or the like to suppress the light energy of the focal point that is not required by the user, or to substantially eliminate such focal point. This will conceivably improve, for example, "halo," which is a phenomenon of a band shaped or ring shaped light occurring around a light source when viewing a far light source at night, "blurred vision," which is a symptom of vision as if being hazed or viewing an object in fog, and the like.

BACKGROUND ART DOCUMENTS

Patent Documents

Patent Document 1: JP-A-2010-158315
Patent Document 2: JP-A-2013-517822
Patent Document 3: WO2013/118176

SUMMARY OF THE INVENTION

Problem the Invention Attempts to Solve

It is an object of the present invention to provide a diffractive multifocal ophthalmic lens with a novel structure which is able to contribute to obtaining a good QOV.

Means for Solving the Problem

Definition or Explanation of Phrases

Following, prior to explaining the present invention, definition or explanation below are described regarding phrases, concepts, etc. used with the present invention.

(1) Pupil Function

A pupil function is a lens characteristic function that describes the physical effect of a lens by which it is possible to change the state of light made incident on the lens, and in specific terms, is represented by the product of the amplitude function A(r) and the exponential function of the phase function φ(r) as noted in Equation 1 below.

$$F(r) = A(r)e^{i\phi(r)} \quad \text{Equation 1}$$

F(r): Pupil function
A(r): Amplitude function
φ(r): Phase function (2) Phase Function A phase function is defined as the function that mathematically expresses the physical effect provided in a lens such as giving changes in the phase of incident light on a lens (position of wave peaks and valleys) using any method. The variable of the phase function is mainly expressed by position r in the radial direction from the center of the lens, and the phase of light made incident on the lens at the point of the position r undergoes a change by the phase function φ(r) and is emitted from the lens. In specific terms, this is represented by an r–φ coordinate system such as shown in FIG. 1. In this specification, phase is noted as φ, and the unit is radians. One wavelength of light is represented as 2π radians, and a half wavelength as π radians, for example. A distribution of phase in the overall area in which the phase function is provided expressed in the same coordinate system is called a phase profile, or is simply called a profile or zone profile. With an r axis of φ=0 as a reference line, this means that the light made incident at the point of φ=0 is emitted without changing the phase. Also, for this reference line, when a positive value is used for φ, this means that progress of the light is delayed by that phase amount, and when a negative value is used for φ, this means that progress of the light is advanced by that phase amount. In an actual ophthalmic lens, a refracting surface for which a diffractive structure is not given corresponds to this reference line (surface). Light undergoes a phase change based on this phase function and is emitted from the lens.

(3) Amplitude Function

An amplitude function is the function expressed by A(r) in Equation 1 noted above. In this specification, this is defined as a function that represents the change in the light transmission amount when passing through a lens. The variable of the amplitude function is represented as position r in the radial direction from the center of the lens, and represents the transmission rate of the lens at the point of position r. Also, the amplitude function is in a range of 0 or greater and 1 or less, which means that light is not transmitted at the point of A(r)=0, and that incident light is transmitted as it is without loss at the point of A(r)=1. In this specification, unless specifically noted otherwise, the amplitude function A(r) is 1.

(4) Zone

In this specification, a zone is used as the minimum unit in a diffractive structure or diffraction grating provided in a lens.

(5) Zone Sequence

A zone sequence is grasped as a set of a plurality of zones that are arranged in the lens radial direction with specific regularity, and is used as a concept of recognizing a multitude of zones by classifying them by a set of a plurality of zones. For example, when the known Fresnel pitch is used as the regularity for a diffractive structure, it is possible to recognize a profile configured by a zone radius $r_n$ determined in Equation 2 below as a zone sequence. Specifically, in Equation 2, if any one of $r_1$, P, or λ, is different, that is interpreted as a different, separate zone sequence. In this specification, the zone sequences are classified by a description noted as a zone sequence (1), a zone sequence (2), . . . , etc. However, the regularity for recognizing the zone sequence is not limited to the Fresnel pitch, but for example, the zone arrangement having equal pitches described in the aforementioned patent document can also be used as one regularity. In this way, the zone sequence can appropriately be grasped as a set of a plurality of zones with regularity such as a zone pitch and a zone mode which are objectively recognizable by appearance.

$$r_n = \sqrt{r_1^2 + \frac{2(n-1)\lambda}{P}} \quad \text{Equation 2}$$

$r_n$: The nth zone radius of a certain zone sequence
$r_1$: The first zone radius of the zone sequence
n: Natural number
P: Addition power based on 1st order diffracted light of the zone sequence
λ: Design wavelength (6) Blaze A blaze is one mode that represents the diffraction grating configuration using phase function, and in addition to specifying each zone that configures the diffraction grating, the blaze specifies the phase change in light waves that pass through the each zone. For example, the blaze indicates the one in which the phase is changing in a roof-like shape. With the present invention, in FIGS. 2A-2D which show the phase on the plane orthogonal to the optical axis in cross section shape, the blaze is basically an item as shown in FIG. 2A for which there is linear change between the peaks (peak point or ridge line) and the valleys (bottom point or valley line) of a shed roof shape in one zone. However, the concept of the blaze shaped phase function of the present invention also includes an item as shown in FIG. 2B for which changes between the peaks and valleys occur in a parabolic curve, and an item as shown in FIG. 2C that appears as an irregular shape (square wave shape), etc. Moreover, as shown in FIG. 2D, an item for which the peaks and valleys are linked so that the change occurs as a part of a sine wave function, and an item for which the peaks and valleys are linked so that the change occurs within an interval with no extrema in a certain function, are also included in the concept of the blaze shaped phase function of the present invention because they function as a diffraction grating for the light waves and generate a plurality of focal points.

In this specification, the peak and valley positions of the blaze for each zone of the diffraction grating is determined using the blaze inclination and the shift from the reference line (plane). Specifically, it is determined using the following constants. First, as shown in FIG. 2A, in the blaze of the ith zone (orbicular zone) in the radial direction from the center of the lens, basically, the absolute values of phase $\phi_{i-1}$ of the position of the inner diameter radius $r_{i-1}$ of the zone and phase $\phi_i$ of the position of the outer diameter radius $r_i$ are set to be equal relative to the reference surface (line), in other words, set to be $|\phi_i|=|\phi_{i-1}|$, and the inclination of the blaze is determined with the phase constant h determined by Equation 3.

$$h = \frac{\phi_{i-1} - \phi_i}{2\pi} \quad \text{Equation 3}$$

Next, the phase shift τ is used to determine the shift in the φ direction of the blaze from the reference line (surface) with the inclination of the blaze maintained as it is. The mode of the blaze to which that shift is given is shown in FIG. 3. When the blaze is shifted upward (plus direction) from the reference line, τ is a positive value, and when it is shifted downward (minus direction) from the reference line, τ is a negative value. The unit of τ is radians. In this specification, where the typical phase notation of the inner diameter radius position and the outer diameter radius position of the zone based on this setting method are respectively $\phi_{i-1}'$ and $\phi_i'$, these are expressed by Equation 4 using the phase constant h and the phase shift τ.

$$\phi_{i-1}' = h \times \pi + \tau$$

$$\phi_i' = -h \times \pi + \tau \quad \text{Equation 4}$$

In specific terms, when the phase constant h=0.5 and the phase shift τ is τ=0, $\phi_{i-1}'$ is determined as 1.5704 radians, and $\phi_i'$ is −1.5704 radians. If there is 1 radian of a phase shift in the positive direction, with τ=1, $\phi_{i-1}'$ is determined as 2.5704 radians, and $\phi_i'$ is −0.5704 radians. Also, when the phase constant is negative, for example when phase constant h is h=−0.5, and τ is τ=0, $\phi_{i-1}'$ is determined as −1.5704 radians, and $\phi_i'$ is 1.5704 radians. That is, this means that when the phase constant is of a positive sign, the blaze becomes a right downward inclination with the r–φ, coordinate system, and when the phase constant is of a negative sign, it becomes a right upward inclination with that coordinate system. In the examples described later as well, the phases of the blaze peak and valley positions are noted using these phase constant and phase shift.

(7) Inclination Angle of Blaze

Considering the fact that, for the Fresnel pitch or the like, for example, the zone pitch changes depending on the radial direction position, or the like, an inclination angle of a blaze is defined by the following equation using the aforementioned phase constant h, which is a blaze inclination angle with respect to the reference surface. Therefore, the unit of the inclination angle is radians/mm².

Inclination angle=$(|h| \times 2 \times \pi)$/zone area (8) Standard Profile

A standard profile refers to a phase profile of a diffractive lens giving a plurality of focal points, and corresponds to a phase profile without an adjustment zone of the present invention according to claim 1 in CLAIMS. Thus, the standard profile is endowed with optical characteristics having peaks of light energy at a plurality of focal point positions on the optical axis of the transmitted light, and is a phase profile giving peaks of light energy at the focal point positions that are not required by a user, or peaks of light energy at the focal point positions that are required by the user but the peak values thereof are too large or too small. The specific mode of the standard profile, which is the phase profile described here, is not limited in any particular way, but is sufficient to have the optical characteristics as described above. That is, the present invention shall not limit as far as the specific mode of the standard profile as the target. Therefore, for example, the known technologies described in the known documents 1 through 3 cited above, or for example, the technology described in the PCT Application No. PCT/JP2014/071113 which is an earlier application of the present applicant to be published shortly and will be a known technology to which the present invention is applicable when published, can also be recognized as one mode that gives the standard profile of the present invention, but the standard profile shall not be limited to such modes.

(9) Present Invention Profile

A present invention profile refers to a mode for which in the present invention according to claim 1 in CLAIMS, by setting the adjustment zone, the mode of the blaze of a specific zone is made different from that of the above-described standard profile. By appearance, the present invention profile is objectively grasped as an item including zones for which inclination directions are mutually reversed in the phase profile. Specifically, the present invention profile is such that in the diffractive multi-focal ophthalmic lens of the structure according to the present invention, the optical characteristics of the diffraction grating are represented using a blaze shaped phase function. Here, a "reversed inclination" of the present invention, specifically, an item for which the inclination of the blaze is reversed, is interpreted as being an item for which the blaze inclination sign (that is, the phase constant sign) is reversed, and does not require that the absolute value of the inclination be the same, and is not limited to being an item which is symmetrically reversed. Besides, the blaze that substantially does not incline by its inclination being set to approximately 0 is one mode of inclination which is reverse to the blazes with any inclination direction in the standard profile. As apparent from the examples described later, for the present invention profile, the existence of the standard profile is not essential. For example, as long as there is a connection zone or the like having a gentle and non-blaze shape for which the inclination angle is so small in comparison with the other blazes as to be recognizable by appearance or the inclination is set to approximately 0, the present invention profile can be identified by the specific phase profile without the need of the existence of the standard profile.

(10) Optical Axis

An optical axis is a rotation symmetrical axis of the diffraction grating in the optical part of the lens, and in this specification, means the axis that goes through the lens center and extends into an object space and an image side space, with the lens geometrical center set to the optical center. The optical axis, which is the rotation symmetrical axis of the lens diffraction grating, can be offset in the radial direction from the lens geometrical center.

(11) 0th Order Focal Point

A 0th order focal point means the focal point position of 0th order diffracted light. Hereafter, +1st order focal point means the focal point position of +1st order diffracted light, +2nd order focal point means the focal point position of +2nd order diffracted light, and so forth.

(12) Intensity Distribution on the Optical Axis

An intensity distribution on the optical axis is such that the intensity of the light after passing through the lens is plotted extending over the optical axis of the image side space. The intensity distribution on the optical axis is the same as the light intensity distribution of the transmitted light in the optical axis direction in this specification, and it can be objectively understood that there exists a focal point at the position which is recognizable as a clear peak by appearance with respect to the intensity distribution on the optical axis. Specifically, it is not required that such focal point is intentionally set with the lens design or the like according to the aforementioned Equation 2 on the assumption that, for example, the conventionally known Fresnel pitch is used. The optical characteristics are exhibited due to the objective existence of the peak, and the present invention can provide the setting effect of the peak level to the peak of the light energy that exists irrespective of whether it is intended or not.

(13) Point Spread Function

A point spread function is the intensity distribution that forms on a certain image plane after light emitted from a point light source passes through a lens, and for which the intensity of the light with respect to the radial distance from the image plane center is plotted. In this specification, the image plane is a projection plane orthogonal to the optical axis. Specifically, the present inventor confirmed that, as described above, halo and blurred vision are grasped as the existence of a small peak group like a stray light that reaches the position away from the image plane center in the radial direction in the point spread function of the image plane at the focal point position required by the user. In order to suppress this small peak group and enhance the QOV at the required focal point position, it is effective to suppress or substantially eliminate the peak of the light energy objectively generated at other position, which is not required or is regarded as relatively unimportant. In this way, by suppressing the peak of the light energy at the specific focal point among the plurality of focal points that are objectively grasped, it is possible to use the present invention for enhancing the QOV at the other focal point position which is required, or the like.

(14) Relief

As one practical and exemplary approach for realizing an ophthalmic lens using the phase function specified by the present invention profile, it is possible to realize a diffraction grating having a desired phase function by giving an actual form to the lens surface comprising a known lens material having a prescribed refractive index. Here, relief is the general term for a micro-uneven shaped structure formed on the lens surface obtained by reflecting the optical path length correlating to the phase determined by the phase profile and specifically converting to an actual form of a lens. A specific conversion formula for converting the blaze shaped phase to relief shape is determined in Equation 5 below, and it is possible to convert a step of the blaze phase to a relief step as an actual form.

$$\text{Relief step} = h \times \frac{\lambda}{n_s - n_m} \quad \text{Equation 5}$$

h: Phase constant
λ: Design wavelength
$n_s$: Refractive index of lens base material
$n_m$: Refractive index of medium covering the lens

MODE OF INVENTION

Here, with the circumstances noted in the Background Art section as the background, the present invention has the purpose of addressing the problems noted in the Problem the Invention Attempts to Solve section, and characteristic modes of the present invention are represented as noted below using the phrases described above under the concept described above.

A first mode of the present invention provides an ophthalmic diffractive multi-focal lens generating at least three focal points in an optical axis direction using a diffractive structure including a phase profile to which a plurality of blaze shaped zones are set in a concentric circle form, the ophthalmic diffractive multi-focal lens being characterized in that: at least one of the zones serves as an adjustment zone for which an inclination direction in the phase profile is reversed with respect to that of other zones; and a light intensity level giving a peak at a position away from the three focal points in a light intensity distribution of transmitted light in the optical axis direction is kept low in comparison with a phase profile without the adjustment zone.

With the present invention, it would also be acceptable to provide the ophthalmic diffractive multi-focal lens according to the first mode, wherein an absolute value of an inclination angle of the adjustment zone in the phase profile is smaller than an absolute value of an inclination angle of the other zones.

A second mode of the present invention provides the ophthalmic diffractive multi-focal lens according to the first mode, wherein an inclination angle of the adjustment zone in the phase profile specified by a following equation is not greater than 20 radians/mm². In the present mode, it would also be conceivable that the inclination angle of the adjustment zone is not greater than 30 radians/mm².

Inclination angle=(absolute value of phase constant×
  2×π)/zone area (unit: radians/mm²)

A third mode of the present invention provides the ophthalmic diffractive multi-focal lens according to the first or second mode, wherein in the phase profile, a phase shift of the adjustment zone is set within a range of −π to +π radians with respect to a reference line of a phase in the phase profile.

A fourth mode of the present invention provides the ophthalmic diffractive multi-focal lens according to any of the first through third modes, wherein in the phase profile, the adjustment zone is set such that the adjustment zone intersects a reference line of a phase in the phase profile.

A fifth mode of the present invention provides the ophthalmic diffractive multi-focal lens according to any of the first through fourth modes, wherein the peak in the light intensity distribution of the transmitted light in the optical axis direction that is kept low in comparison with the phase profile without the adjustment zone is a peak that exists within a range of ±5 diopters (or abbreviated as "D") with respect to a focal point position of at least one of the three focal points in optical characteristics given by the phase profile without the adjustment zone, and is a peak that has a peak level which is not less than one-third of that of at least one of the three focal points.

A sixth mode of the present invention provides the ophthalmic diffractive multi-focal lens according to any of the first through fifth modes, wherein a peak level of the peak in the light intensity distribution of the transmitted light in the optical axis direction that is kept low in comparison with the phase profile without the adjustment zone is not greater than 50% of all peak levels of the three focal points.

A seventh mode of the present invention provides the ophthalmic diffractive multi-focal lens according to any of the first through sixth modes, wherein the phase profile has a periodic structure of zone groups repeated in a radial direction, the zone groups comprising a certain number of the zones, and the zones that correspond in at least two of the zone groups each serve as the adjustment zone.

An eighth mode of the present invention provides the ophthalmic diffractive multi-focal lens according to any of the first through seventh modes, wherein the phase profile set in the concentric circle form is set based on a Fresnel pitch.

A ninth mode of the present invention provides the ophthalmic diffractive multi-focal lens according to any of the first through eighth modes, wherein the phase profile to which the plurality of blaze shaped zones generating at least three focal points in the optical axis direction are set in the concentric circle form using the diffractive structure serves as an adjusted profile, the adjusted profile being dividable into starting profiles that are a plurality of phase profiles configured to be overlapped each other, and the adjusted profile being a composite profile generated by the phase profiles being overlapped, and at least one of the zones of the composite profile serves as the adjustment zone for which an inclination direction has a different blaze shape from an overlapping of the starting profiles.

A tenth mode of the present invention provides the ophthalmic diffractive multi-focal lens according to any of the first through ninth modes, wherein the blaze shaped phase profile is expressed by Equation 6.

$$\phi(r) = \frac{\phi'_i - \phi'_{i-1}}{r_i - r_{i-1}} \times r + \frac{\phi'_{i-1} \times r_i - \phi'_i \times r_{i-1}}{r_i - r_{i-1}} \quad \text{Equation 6}$$

r: Radial distance from the lens center
$r_{i-1}$: Inner diameter (radius) of the ith zone
$r_i$: Outer diameter (radius) of the ith zone
$\phi_{i-1}'$: Phase at the inner diameter (radius) position of the ith zone
$\phi_i'$: Phase at the outer diameter (radius) position of the ith zone An eleventh mode of the present invention provides the ophthalmic diffractive multi-focal lens according to any of the first through tenth modes, wherein a reduction ratio in a light intensity level due to the adjustment zone for a light intensity peak that is fourth highest in the light intensity level after the three focal points is greater than reduction ratios in light intensity levels due to the adjustment zone for light intensity peaks of the three focal points.

A twelfth mode of the present invention provides an ophthalmic diffractive multi-focal lens generating at least three focal points in an optical axis direction using a diffractive structure including a phase profile to which a plurality of blaze shaped zones are set in a concentric circle form, the ophthalmic diffractive multi-focal lens being characterized in that: the phase profile has a structure of zone groups repeated in a radial direction, the zone groups comprising a certain number of the zones; areas of annular regions occupied by the zone groups that are repeated are equal to each other; and a connection zone having a gentle and non-blaze shape is formed between the zone groups adjacent to each other.

In the present mode, the annular area occupied by each zone group is grasped not as an actual area of the inclined surface but as an area projected to a prescribed reference surface. As a specific example, the surface such as a refracting surface for which the phase is φ=0, namely, the incident light is transmitted and emitted without the phase change, is regarded as a reference surface, and the annular area is grasped by the area projected with respect to the reference surface in the normal direction. However, for the lenses having a small refractive power, it would also be acceptable to regard the surface orthogonal to the optical axis as the reference surface.

Additionally, in the present mode, it is not necessary for the repeated structure of a certain number of zones that constitute the repeated zone groups to have a phase profile for which all the repeated zone groups completely correspond. For example, only to a specific zone group, a special diffractive zone that does not exist in other zone group regions may be added. Also, a region comprising an independent diffractive zone that does not belong to any zone group may be added to a specific position such as the central region including the optical axis.

A thirteenth mode of the present invention provides the ophthalmic diffractive multi-focal lens according to the twelfth mode, wherein the connection zone is set with an inclination reverse to an inclination direction of the blaze shaped phase profile that constitutes the zone groups such that the connection zone is set with a phase profile for which none of a peak point and a valley bottom point is included.

A fourteenth mode of the present invention provides an ophthalmic diffractive multi-focal lens generating at least three focal points in an optical axis direction using a diffractive structure including a phase profile to which a plurality of blaze shaped zones are set in a concentric circle form, the ophthalmic diffractive multi-focal lens being characterized in that: the phase profile has a combined structure of a plurality of zone sequences for which the zone sequences comprising a plurality of zones formed with prescribed regularity in a radial direction are overlapped; and one of the zone sequences serves as a connection zone including a phase profile having a gentle and non-blaze shape.

A fifteenth mode of the present invention provides the ophthalmic diffractive multi-focal lens according to the fourteenth mode, wherein the connection zone is set with an inclination reverse to an inclination direction of the blaze shaped phase profile of another of the zone sequences that is different from the zone sequence to which the connection zone belongs such that the connection zone is set with a phase profile for which none of a peak point and a valley bottom point is included.

The zone sequences in the present mode can be grasped as an item such that, for example, as shown in FIG. 4, which hypothetically shows the peak point positions of the phase profile with solid lines or dashed lines on a circular plane simulating a lens, the standard profile constituted with the diffractive structure having the phase profile that gives multiple focal points is divided into two zone sequences here, which are a plurality of zone sequences each having prescribed regularity such as the Fresnel pitch.

A sixteenth mode of the present invention provides a method for manufacturing an ophthalmic diffractive multi-focal lens capable of generating at least three focal points in an optical axis direction using a diffractive structure comprising a plurality of zones in a concentric circle form, the method being characterized by: setting a phase profile for which the zones have a blaze shape inclining in a same direction, the phase profile generating the at least three focal points; and reducing a light intensity level giving a peak at a position away from the three focal points in a light intensity distribution of transmitted light in the optical axis direction by setting an adjustment zone for which an inclination direction of at least one of the zones of the phase profile is reversed with respect to that of other zones.

Effect of the Invention

As will be understood from the above explanation and examples to be described later, according to the present invention, it is possible to realize the diffractive multi-focal ophthalmic lens of novel structure which is capable of suppressing halo and enhancing the quality of vision in comparison with the diffractive multi-focal ophthalmic lens of conventional structure.

BRIEF DESCRIPTION OF THE DRAWINGS

FIG. 1 is a graph of a phase function in the r–φ coordinate system with the phase φ of a phase modulation structure provided in the diffractive lens expressed as the relationship with the lens radial direction position r.

EMBODIMENTS FOR CARRYING OUT THE INVENTION

Following, the present invention will be more specifically clarified by describing embodiments for carrying out the invention. First, methods and conditions, etc., for calculation simulation used by the following examples are explained.

Simulation of the Intensity Distribution on the Optical Axis

With simulation of the intensity distribution on the optical axis, for the calculation software, an item was used that can calculate amplitude distribution and intensity distribution from each zone based on a diffraction integral equation derived from a theory known in the field called the scalar diffraction theory. Using this calculation software, we calculated the intensity distribution on the optical axis. A far point light source was set up as light source for calculation, and the calculation was performed on the assumption that parallel light beams in the same phase enter into the lens. Also, in the calculation, it was assumed that the media on the object and image sides are vacuum and the lens is an ideal lens having no aberration (light beams passing through the lens form an image at the same focal point regardless of the emitting position of the light). Further, the calculation was performed based on the assumption that the wavelength equals 546 nm and the refractive power of the lens for the 0th order diffracted light (basic refractive power) equals 7 D.

Also, in the examples below, unless otherwise specified, calculation was performed with the blaze as a linear function, and expressed by the function determined by Equation 7 below.

$$\phi(r) = \frac{\phi'_i - \phi'_{i-1}}{r_i - r_{i-1}} \times r + \frac{\phi'_{i-1} \times r_i - \phi'_i \times r_{i-1}}{r_i - r_{i-1}} \qquad \text{Equation 7}$$

r: Radial distance from the lens center
$r_{i-1}$: Inner diameter (radius) of the ith zone
$r_i$: Outer diameter (radius) of the ith zone
$\phi_{i-1}'$: Phase at the inner diameter (radius) position of the ith zone
$\phi_i'$: Phase at the outer diameter (radius) position of the ith zone The intensity distribution on the optical axis was such that the distance on the optical axis from the lens position as the base point to the image plane was converted to diopters, the focal point position of the 0th order diffracted light was standardized as 0 D, and the intensity was plotted on that standardized scale. The lens aperture range for which the calculation simulation was performed, unless otherwise specified, was the region up to the zone number described in each example.

During explaining specific examples of the present invention obtained based on the method and conditions of the calculation simulation as described above based on examples, first, an outline is given of the structure and characteristics of the diffractive lens based on the present invention.

Figure 5:
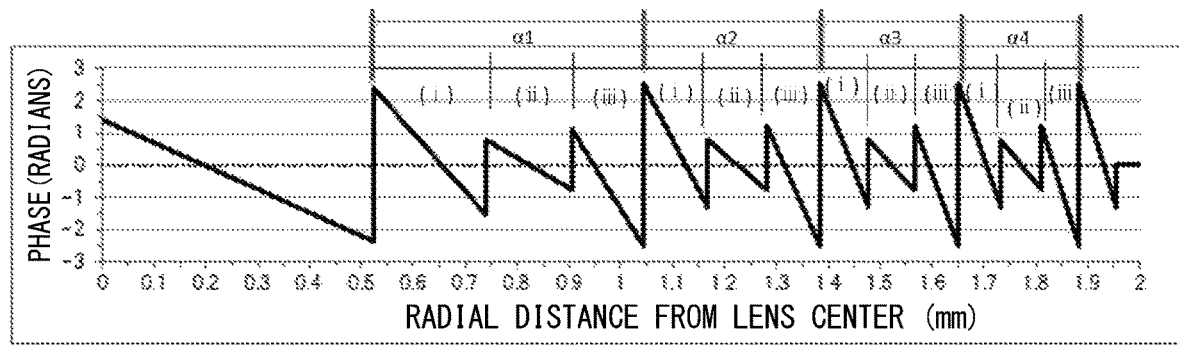
FIG. 5 is a drawing showing a phase profile which is a standard profile contrasted with the diffractive multi-focal ophthalmic lens according to the present invention.

In Table 1 and FIG. 5, an example is shown of the standard profile which is the base of the diffractive structure of the present invention. The standard profile has a zone structure in which zone radii determined based on the Fresnel pitch equation of Equation 8 are arranged in a concentric circle form with the design wavelength being 546 nm and the addition power being P=4 D, and has a structure in which the blaze shape is determined by the phase constants and the phase shifts shown in Table 1.

$$r_i = \sqrt{\frac{2i\lambda}{P}}$$ Equation 8

$r_i$: The ith zone radius of a certain zone sequence
i: Natural number
P: Addition power based on 1st order diffracted light of the zone sequence
$\lambda$: Design wavelength

TABLE 1

| Zone No. i | Zone radius $r_i$ (mm) | Phase constant h | Phase shift $\tau$ (radians) |
|---|---|---|---|
| 1 | 0.5225 | 0.60 | −0.47 |
| 2 | 0.7389 | 0.63 | 0.44 |
| 3 | 0.9050 | 0.25 | 0 |
| 4 | 1.0450 | 0.58 | −0.69 |
| 5 | 1.1683 | 0.61 | 0.60 |
| 6 | 1.2798 | 0.25 | 0 |
| 7 | 1.3824 | 0.59 | −0.66 |
| 8 | 1.4778 | 0.61 | 0.61 |
| 9 | 1.5675 | 0.25 | 0 |
| 10 | 1.6523 | 0.59 | −0.65 |
| 11 | 1.7329 | 0.60 | 0.61 |
| 12 | 1.8100 | 0.25 | 0 |
| 13 | 1.8839 | 0.60 | −0.64 |
| 14 | 1.9550 | 0.60 | 0.62 |

Figure 6:
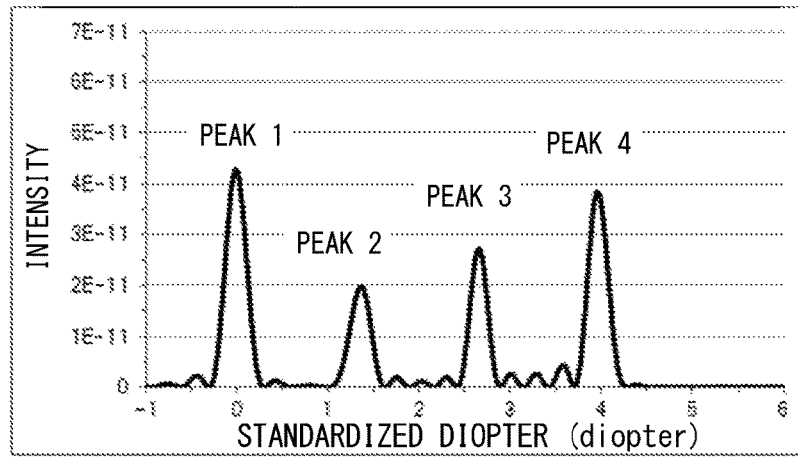
FIG. 6 is a drawing showing an intensity distribution on the optical axis which is an optical characteristic of the ophthalmic lens having the standard profile shown in FIG. 5.

FIG. 6 shows the intensity distribution on the optical axis of this standard profile. With this standard profile, Peak 1 is generated at the 0 D position based on the 0th order diffracted light, Peak 2 at approximately the 1.33 D position, Peak 3 at approximately the 2.67 D position, and Peak 4 at the 4 D position, thereby generating four peaks in total for forming main focal points.

When this lens is applied as an intraocular lens, for example, the intraocular lens is configured such that the 0 D peak acts as a focal point for far vision, the 1.33 D peak can be used as a focal point for which objects of approximately 1.5 to 2 m in front can be seen, the 2.67 D peak can be used as a focal point for which objects of approximately 50 to 60 cm in front can be seen, and also, the 4 D peak can be used as a focal point for which objects of approximately 35 to 40 cm in front can be seen. Such intraocular lens is useful as a multi-focal intraocular lens with which objects can be seen in a wide range from the near region for reading to the far region.

The far region is a basic and important region when people see the objects. The near region is an important region in everyday life beginning with reading, viewing a mobile tablet, sewing, cooking, and so forth. Besides, in recent years, there are increasing opportunities to view a personal computer screen, and visibility for objects in a region of 50 to 60 cm in front becomes more important. Greater importance is being placed on ensuring visions for these regions as well as enhancing the quality of vision.

Turning to the ophthalmic lens comprising the standard profile as well, it is necessary to suitably modulate the peak intensities of these regions, namely, Peaks 1, 2, 3, and 4 in FIG. 6 and make the ophthalmic lens suitable for intended uses by patients and users. Also, in some instances, in order to suppress halo which tends to be a problem during far vision such as night driving and enhance the quality of vision at Peak 1 giving a focal point for far vision, it is necessary to suppress or substantially eliminate the level of Peak 2 or the like which is relatively less important for the users.

Each of examples of the present invention described below is an exemplary mode of the ophthalmic diffractive multi-focal lens of novel structure in which the diffractive lens, which gives at least three focal point peaks in light of such background or circumstances, is able to reduce the peak intensity at the position away from the three focal points depending on the regions for viewing objects, and more preferably, is able to increase at least one of the three peak intensities.

Example 1

In Example 1, among the four focal point peaks given by the standard profile, the amount of light distributed to Peak 2 is reduced. Besides, the light energy peaks of the focal point positions other than Peak 2 are increased.

Figure 7:
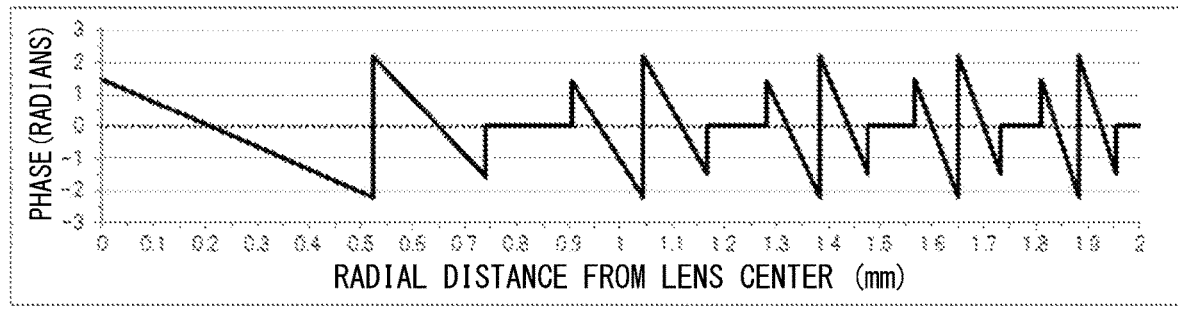
FIG. 7 is a drawing showing a phase profile which is a present invention profile of the diffractive multi-focal ophthalmic lens as Example 1 of the present invention.

In Example 1, the zone radius is set equal to that of the standard profile, and the phase constants and the phase shifts shown in Table 2 are newly set. Specifically, the zones of zone numbers 3, 6, 9, and 12 are the adjustment zones with the phase constant and the phase shift set to zero. Details of the phase profile of Example 1 are shown in FIG. 7 and Table 2.

TABLE 2

| Zone No. i | Phase constant h | Phase shift $\tau$ (radians) |
|---|---|---|
| 1 | 0.58 | −0.37 |
| 2 | 0.60 | 0.32 |
| 3 | 0 | 0 |
| 4 | 0.57 | −0.40 |
| 5 | 0.59 | 0.35 |
| 6 | 0 | 0 |
| 7 | 0.58 | −0.38 |
| 8 | 0.59 | 0.35 |
| 9 | 0 | 0 |
| 10 | 0.58 | −0.38 |
| 11 | 0.59 | 0.36 |
| 12 | 0 | 0 |
| 13 | 0.58 | −0.37 |
| 14 | 0.59 | 0.36 |

The zones of zone numbers 3, 6, 9, and 12 that serve as the adjustment zones have the inclination angle of 0, which is one mode in which the inclination direction is reversed with respect to the blaze of the standard profile of FIG. 5. In the present embodiment in particular, the phase is set on the reference surface.

Figure 8:
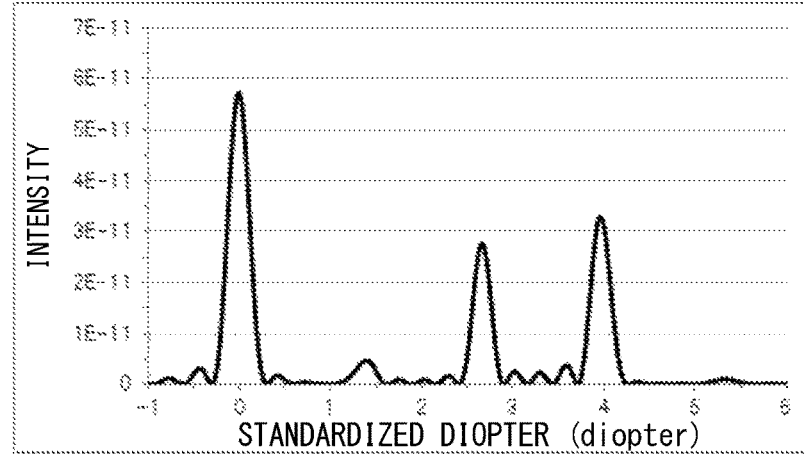
FIG. 8 is a drawing showing an intensity distribution on the optical axis which is an optical characteristic of an ophthalmic lens having the phase profile shown in FIG. 7 as Example 1 of the present invention.

The intensity distribution on the optical axis of Example 1 is shown in FIG. 8. Additionally, for each peak, the intensity before and after arranging the adjustment zone as well as the intensity change ratio are shown in Table 3.

TABLE 3

Peak intensity change of Example 1 before and after adjustment

|  |  | Peak | | | |
| --- | --- | --- | --- | --- | --- |
|  |  | 1 | 2 | 3 | 4 |
| Peak intensity ($\times 10^{11}$) | Before adjustment | 4.28 | 1.99 | 2.72 | 3.84 |
|  | After adjustment | 5.72 | 0.48 | 2.78 | 3.29 |
| Intensity change ratio (%) | | 34 | −76 | 2 | −14 |

With the lens including the adjustment zone of Example 1, we can see that, in comparison with the lens of the standard profile without the adjustment zone, the intensity of Peak 2 is considerably reduced, and the peak is substantially eliminated by being reduced to as far as a noise-like level. Moreover, in the present example, we can see that the reduced amount of the light energy of Peak 2 is mainly distributed to Peak 1 for far vision, increasing its intensity. The lens after the adjustment is able to provide an ophthalmic lens with more enhanced far vision.

Example 2

Figure 9:
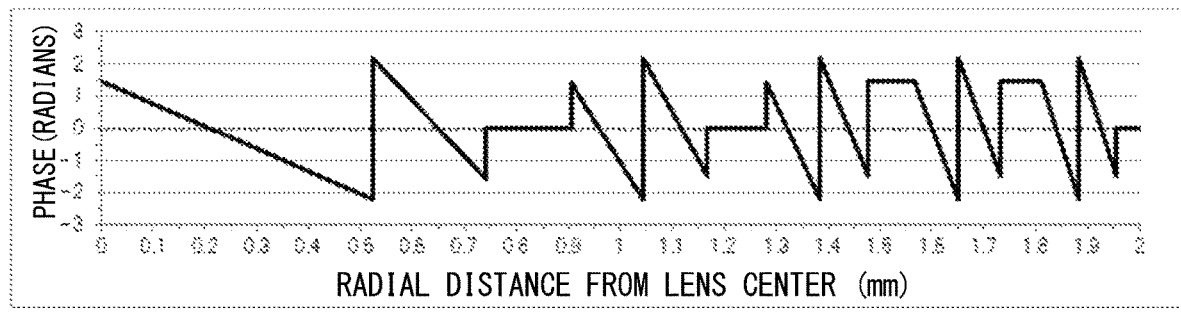
FIG. 9 is a drawing showing a phase profile which is a present invention profile of the diffractive multi-focal ophthalmic lens as Example 2 of the present invention.

In Example 2, the zones of zone numbers 9 and 12 of Example 1 are set with the phase constants and the phase shifts shown in Table 4. The phase profile including such adjustment zone is shown in FIG. 9. With the phase constants of the 9th and 12th zones kept zero, the peak point positions of the adjacent outer zones are set to be aligned therewith.

TABLE 4

| Zone No. i | Phase constant h | Phase shift τ (radians) |
| --- | --- | --- |
| 1 | 0.58 | −0.37 |
| 2 | 0.60 | 0.32 |
| 3 | 0 | 0 |
| 4 | 0.57 | −0.40 |
| 5 | 0.59 | 0.35 |
| 6 | 0 | 0 |
| 7 | 0.58 | −0.38 |
| 8 | 0.59 | 0.35 |
| 9 | 0 | 1.45 |
| 10 | 0.58 | −0.38 |
| 11 | 0.59 | 0.36 |
| 12 | 0 | 1.45 |
| 13 | 0.58 | −0.37 |
| 14 | 0.59 | 0.36 |

Figure 10:
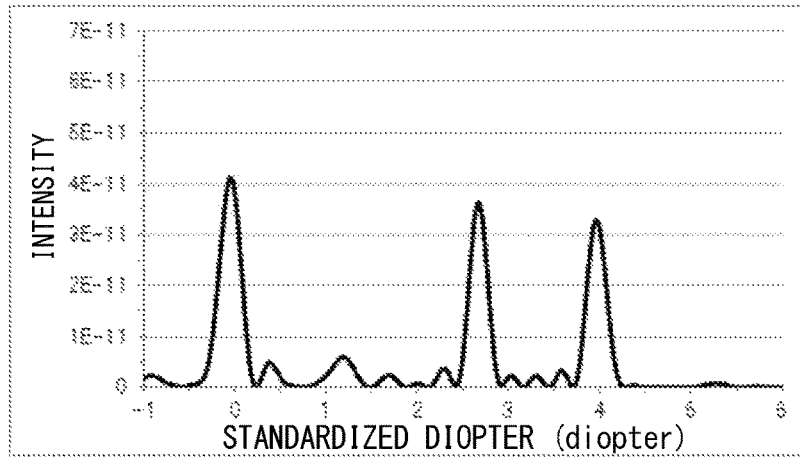
FIG. 10 is a drawing showing an intensity distribution on the optical axis which is an optical characteristic of an ophthalmic lens having the phase profile shown in FIG. 9 as Example 2 of the present invention.

The intensity distribution on the optical axis of Example 2 is shown in FIG. 10. The peak intensity before and after adjustment as well as the intensity change ratio are shown in Table 5. The intensity of Peak 2 is considerably reduced, and the reduced amount of its intensity is distributed to Peak 3 as the increased amount of its intensity. Thus, such ophthalmic lens is a lens which is advantageous for personal computer work or the like.

TABLE 5

Peak intensity change of Example 2 before and after adjustment

|  |  | Peak | | | |
| --- | --- | --- | --- | --- | --- |
|  |  | 1 | 2 | 3 | 4 |
| Peak intensity ($\times 10^{11}$) | Before adjustment | 4.28 | 1.99 | 2.72 | 3.84 |
|  | After adjustment | 4.12 | 0.61 | 3.63 | 3.28 |
| Intensity change ratio (%) | | −4 | −70 | 34 | −15 |

Example 3

Figure 11:
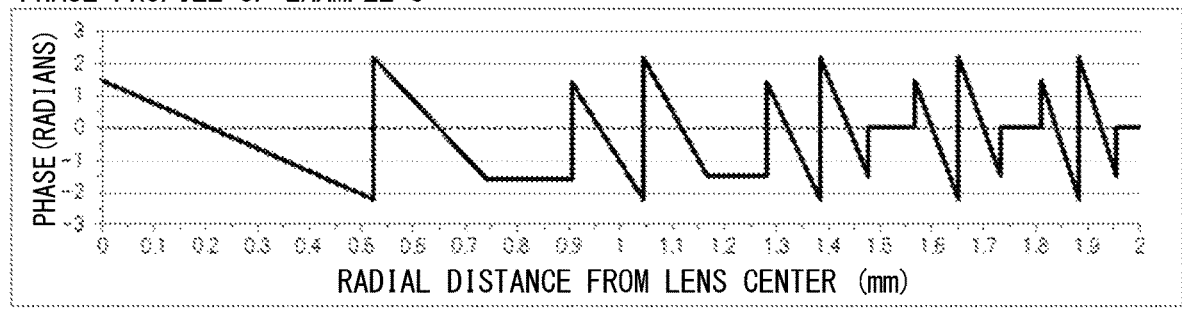
FIG. 11 is a drawing showing a phase profile which is a present invention profile of the diffractive multi-focal ophthalmic lens as Example 3 of the present invention.

In Example 3, the phase constants and the phase shifts of the zones of zone numbers 3 and 6 of Example 1 are set with the values shown in Table 6. Specifically, the inclinations of the 3rd and 6th zones are set to zero, thereby serving as the adjustment zones so as to be aligned with the valleys of the adjacent inner zones. Details of the phase profile of Example 3 are shown in FIG. 11.

TABLE 6

| Zone No. i | Phase constant h | Phase shift τ (radians) |
| --- | --- | --- |
| 1 | 0.58 | −0.37 |
| 2 | 0.60 | 0.32 |
| 3 | 0 | −1.57 |
| 4 | 0.57 | −0.40 |
| 5 | 0.59 | 0.35 |
| 6 | 0 | −1.50 |
| 7 | 0.58 | −0.38 |
| 8 | 0.59 | 0.35 |
| 9 | 0 | 0 |
| 10 | 0.58 | −0.38 |
| 11 | 0.59 | 0.36 |
| 12 | 0 | 0 |
| 13 | 0.58 | −0.37 |
| 14 | 0.59 | 0.36 |

Figure 12:
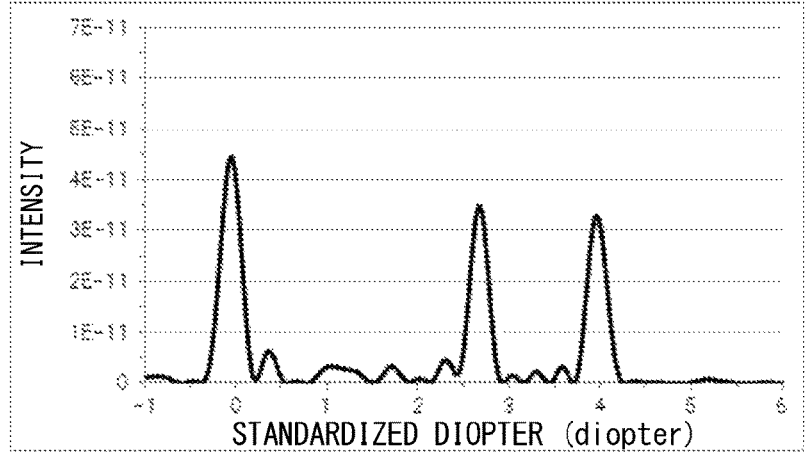
FIG. 12 is a drawing showing an intensity distribution on the optical axis which is an optical characteristic of an ophthalmic lens having the phase profile shown in FIG. 11 as Example 3 of the present invention.

The intensity distribution on the optical axis of Example 3 is shown in FIG. 12. The peak intensity before and after adjustment as well as the intensity change ratio are shown in Table 7. The intensity of Peak 2 is considerably reduced, and the reduced amount of its intensity is distributed to Peak 3 as the increased amount of its intensity. Thus, such ophthalmic lens is a lens which is advantageous for personal computer work or the like.

TABLE 7

Peak intensity change of Example 3 before and after adjustment

|  |  | Peak | | | |
| --- | --- | --- | --- | --- | --- |
|  |  | 1 | 2 | 3 | 4 |
| Peak intensity ($\times 10^{11}$) | Before adjustment | 4.28 | 1.99 | 2.72 | 3.84 |
|  | After adjustment | 4.45 | 0.34 | 3.49 | 3.28 |
| Intensity change ratio (%) | | 4 | −83 | 28 | −15 |

Example 4

In Example 4, the phase constants and the phase shifts of the zones of zone numbers 3, 6, 9, and 12 of Example 1 are set with the values shown in Table 8. Specifically, the inclinations of the 3rd, 6th, 9th, and 12th zones that are made horizontal in Example 1 are slightly reversed with respect to the inclinations of other zones.

TABLE 8

| Zone No. i | Phase constant h | Phase shift τ (radians) |
|---|---|---|
| 1 | 0.58 | −0.37 |
| 2 | 0.60 | 0.32 |
| 3 | −0.05 | 0 |
| 4 | 0.57 | −0.40 |
| 5 | 0.59 | 0.35 |
| 6 | −0.05 | 0 |
| 7 | 0.58 | −0.38 |
| 8 | 0.59 | 0.35 |
| 9 | −0.05 | 0 |
| 10 | 0.58 | −0.38 |
| 11 | 0.59 | 0.36 |
| 12 | −0.05 | 0 |
| 13 | 0.58 | −0.37 |
| 14 | 0.59 | 0.36 |

Figure 13:
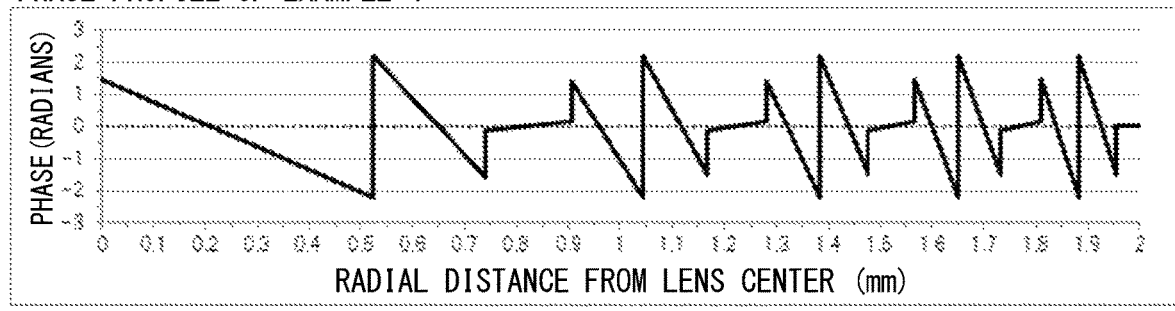
FIG. 13 is a drawing showing a phase profile which is a present invention profile of the diffractive multi-focal ophthalmic lens as Example 4 of the present invention.
Figure 14:
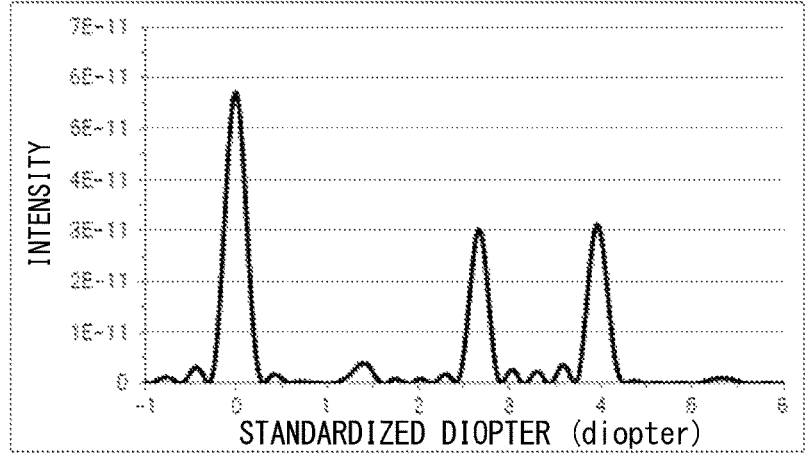
FIG. 14 is a drawing showing an intensity distribution on the optical axis which is an optical characteristic of an ophthalmic lens having the phase profile shown in FIG. 13 as Example 4 of the present invention.

Details of the phase profile of Example 4 are shown in FIG. 13. The intensity distribution on the optical axis of Example 4 is shown in FIG. 14, while the peak intensity before and after adjustment as well as the intensity change ratio are shown in Table 9. The intensity of Peak 2 is considerably reduced, and the reduced amount of its intensity is distributed to Peak 1 and Peak 3 as the increased amount of their intensities. Thus, such ophthalmic lens is a lens which provides more enhanced far vision, and is advantageous for personal computer work or the like as well.

TABLE 9

Peak intensity change of Example 4 before and after adjustment

| | | Peak | | | |
|---|---|---|---|---|---|
| | | 1 | 2 | 3 | 4 |
| Peak intensity (×10$^{11}$) | Before adjustment | 4.28 | 1.99 | 2.72 | 3.84 |
| | After adjustment | 5.70 | 0.41 | 3.03 | 3.11 |
| Intensity change ratio (%) | | 33 | −80 | 11 | −19 |

Example 5

Figure 15:
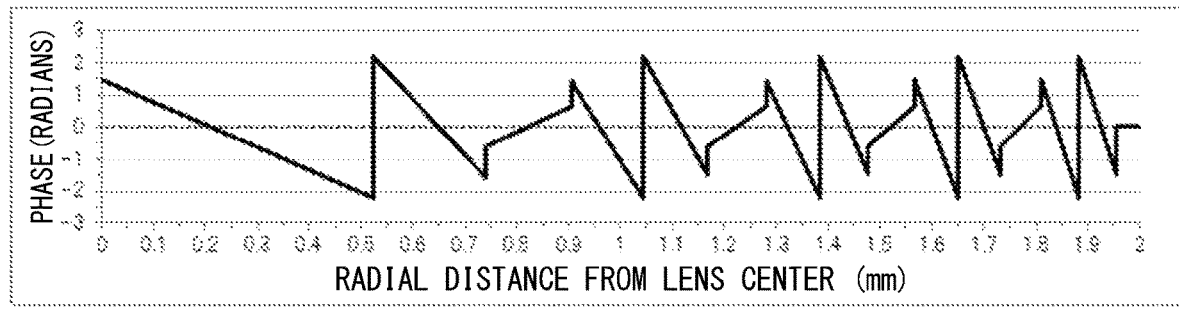
FIG. 15 is a drawing showing a phase profile which is a present invention profile of the diffractive multi-focal ophthalmic lens as Example 5 of the present invention.

In Example 5, the inclinations of the adjustment zones of zone numbers 3, 6, 9, and 12 of Example 4, for which the inclinations are reversed, are made larger. Details of the phase profile of Example 5 are shown in FIG. 15 and Table 10.

TABLE 10

| Zone No. i | Phase constant h | Phase shift τ (radians) |
|---|---|---|
| 1 | 0.58 | −0.37 |
| 2 | 0.60 | 0.32 |
| 3 | −0.2 | 0 |
| 4 | 0.57 | −0.40 |
| 5 | 0.59 | 0.35 |
| 6 | −0.2 | 0 |
| 7 | 0.58 | −0.38 |
| 8 | 0.59 | 0.35 |
| 9 | −0.2 | 0 |

TABLE 10-continued

| Zone No. i | Phase constant h | Phase shift τ (radians) |
|---|---|---|
| 10 | 0.58 | −0.38 |
| 11 | 0.59 | 0.36 |
| 12 | −0.2 | 0 |
| 13 | 0.58 | −0.37 |
| 14 | 0.59 | 0.36 |

Figure 16:
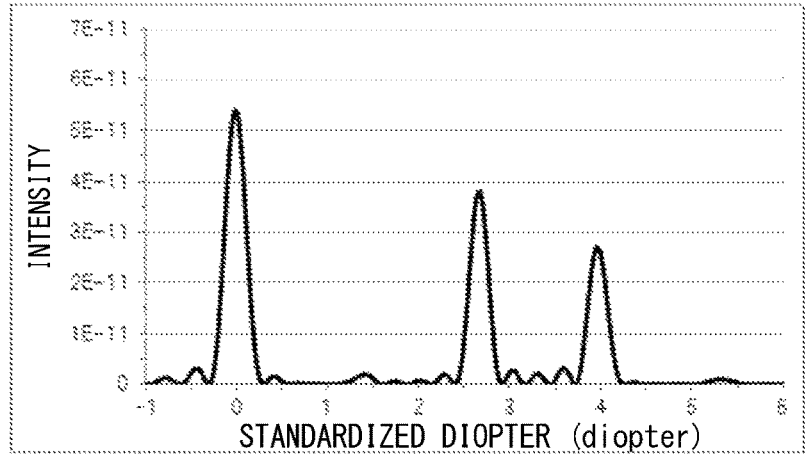
FIG. 16 is a drawing showing an intensity distribution on the optical axis which is an optical characteristic of an ophthalmic lens having the phase profile shown in FIG. 15 as Example 5 of the present invention.

Besides, the intensity distribution on the optical axis is shown in FIG. 16, while the peak intensity before and after adjustment as well as the intensity change ratio are shown in Table 11.

TABLE 11

Peak intensity change of Example 5 before and after adjustment

| | | Peak | | | |
|---|---|---|---|---|---|
| | | 1 | 2 | 3 | 4 |
| Peak intensity (×10$^{11}$) | Before adjustment | 4.28 | 1.99 | 2.72 | 3.84 |
| | After adjustment | 5.40 | 0.20 | 3.80 | 2.71 |
| Intensity change ratio (%) | | 26 | −90 | 40 | −29 |

As will be understood from the intensity distribution on the optical axis of FIG. 16, in the present example, the intensity of Peak 2 is considerably reduced, and the reduced amount of its intensity is distributed to Peak 3 and Peak 1 as the increased amount of their intensities. Thus, the lens of Example 5 is a lens which provides enhanced quality of vision during personal computer work as well as enhanced far vision.

Example 6

Figure 17:
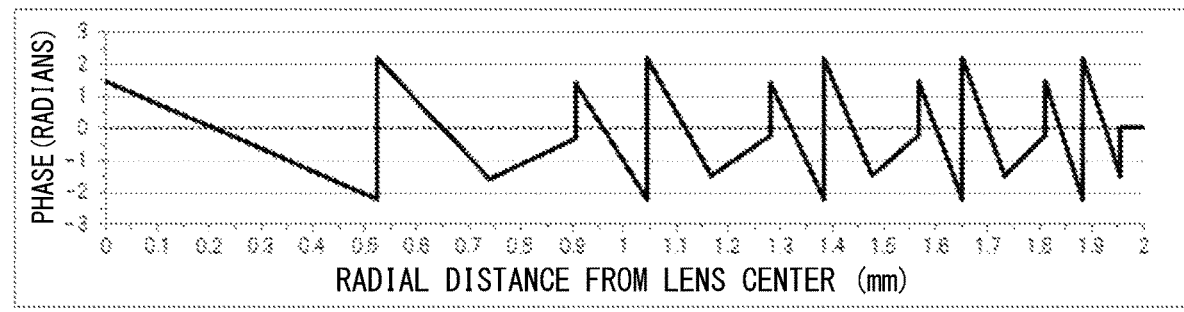
FIG. 17 is a drawing showing a phase profile which is a present invention profile of the diffractive multi-focal ophthalmic lens as Example 6 of the present invention.

In Example 6, the inclinations of the zones which serve as the adjustment zone in Example 5 are kept unchanged, while their phase shifts are modulated so as to be aligned with the valleys of the adjacent inner zones. Details of such phase profile are shown in FIG. 17 and Table 12.

TABLE 12

| Zone No. i | Phase constant h | Phase shift τ (radians) |
|---|---|---|
| 1 | 0.58 | −0.37 |
| 2 | 0.60 | 0.32 |
| 3 | −0.2 | −0.94 |
| 4 | 0.57 | −0.40 |
| 5 | 0.59 | 0.35 |
| 6 | −0.2 | −0.88 |
| 7 | 0.58 | −0.38 |
| 8 | 0.59 | 0.35 |
| 9 | −0.2 | −0.86 |
| 10 | 0.58 | −0.38 |
| 11 | 0.59 | 0.36 |
| 12 | −0.2 | −0.85 |
| 13 | 0.58 | −0.37 |
| 14 | 0.59 | 0.36 |

Figure 18:
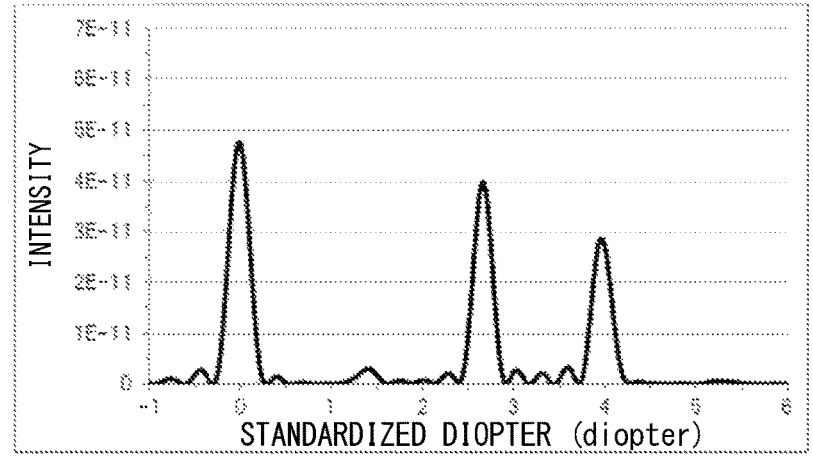
FIG. 18 is a drawing showing an intensity distribution on the optical axis which is an optical characteristic of an ophthalmic lens having the phase profile shown in FIG. 17 as Example 6 of the present invention.

Besides, the intensity distribution on the optical axis is shown in FIG. 18, while the peak intensity before and after adjustment as well as the intensity change ratio are shown in Table 13.

TABLE 13

Peak intensity change of Example 6 before and after adjustment

|  |  | Peak | | | |
|---|---|---|---|---|---|
|  |  | 1 | 2 | 3 | 4 |
| Peak intensity ($\times 10^{11}$) | Before adjustment | 4.28 | 1.99 | 2.72 | 3.84 |
|  | After adjustment | 4.76 | 0.31 | 3.97 | 2.87 |
| Intensity change ratio (%) |  | 11 | −84 | 46 | −25 |

As will be understood from the intensity distribution on the optical axis of FIG. 18, in the present example, the intensity of Peak 2 is considerably reduced, and the reduced amount of its intensity is distributed to Peak 3 and Peak 1 as the increased amount of their intensities. Thus, the lens of Example 6 is a lens which provides enhanced quality of vision during personal computer work as well as enhanced far vision.

Example 7

Figure 19:
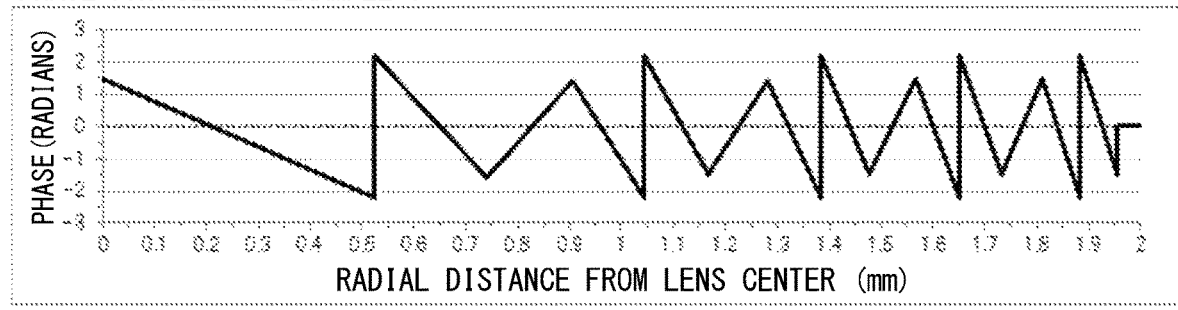
FIG. 19 is a drawing showing a phase profile which is a present invention profile of the diffractive multi-focal ophthalmic lens as Example 7 of the present invention.

Example 7 has a structure in which the ends of the blaze of the zones of zone numbers 3, 6, 9, and 12 that serve as the adjustment zones are arranged so as to be aligned with the valley of the adjacent inner zone and the peak point of the adjacent outer zone. Details of such phase profile are shown in FIG. 19 and Table 14.

TABLE 14

| Zone No. i | Phase constant h | Phase shift τ (radians) |
|---|---|---|
| 1 | 0.58 | −0.37 |
| 2 | 0.60 | 0.32 |
| 3 | −0.47 | −0.08 |
| 4 | 0.57 | −0.40 |
| 5 | 0.59 | 0.35 |
| 6 | −0.47 | −0.03 |
| 7 | 0.58 | −0.38 |
| 8 | 0.59 | 0.35 |
| 9 | −0.47 | −0.02 |
| 10 | 0.58 | −0.38 |
| 11 | 0.59 | 0.36 |
| 12 | −0.47 | −0.02 |
| 13 | 0.58 | −0.37 |
| 14 | 0.59 | 0.36 |

Figure 20:
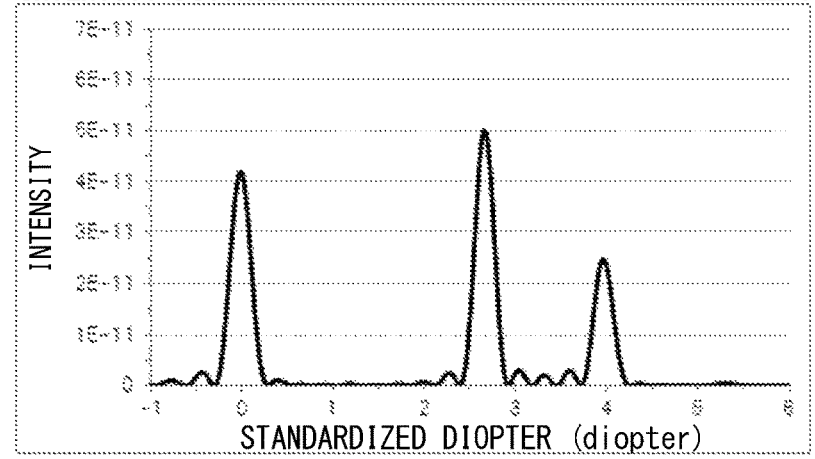
FIG. 20 is a drawing showing an intensity distribution on the optical axis which is an optical characteristic of an ophthalmic lens having the phase profile shown in FIG. 19 as Example 7 of the present invention.

Besides, the intensity distribution on the optical axis is shown in FIG. 20, while the peak intensity before and after adjustment as well as the intensity change ratio are shown in Table 15.

TABLE 15

Peak intensity change of Example 7 before and after adjustment

|  |  | Peak | | | |
|---|---|---|---|---|---|
|  |  | 1 | 2 | 3 | 4 |
| Peak intensity ($\times 10^{11}$) | Before adjustment | 4.28 | 1.99 | 2.72 | 3.84 |
|  | After adjustment | 4.19 | 0.04 | 5.00 | 2.48 |
| Intensity change ratio (%) |  | −2 | −98 | 84 | −35 |

As will be understood from the intensity distribution on the optical axis of FIG. 20, in the present example, the intensity of Peak 2 is considerably reduced, and the reduced amount of its intensity is mainly distributed to Peak 3 as the increased amount of its intensity. Thus, the lens of Example 7 is an ophthalmic lens which provides enhanced quality of vision during personal computer work.

Meanwhile, the preceding Example 1 or the like can also be grasped as the diffractive multi-focal lens by itself that has the present invention profile comprising a specific phase profile described in FIG. 7 or the like without taking the standard profile into consideration. Specifically, in the lens of Example 1, the phase profile has a structure of zone groups α repeated in the radial direction, the zone groups α comprising a certain number (three) of the zone sequences (i), (ii), and (iii). The first zone, which is positioned at the center portion including the optical axis, is grasped as an irregular zone that does not belong to any zone sequence. A plurality of zone groups α1 to α4 that are repeated in the radial direction are set with the radial pitch such that the areas of annular regions around the optical axis of the lens center projected on the reference surface (depicted by the line of phase 0 in FIG. 5) are equal to each other.

Here, the zone sequence (ii) has a gentle and non-blaze shape in which the phase constant is set to 0 so that the blaze substantially does not exist and extends roughly parallel to the reference surface, and can be grasped as a connection zone that connects the phase planes of the adjacent blaze shaped zones of the zone sequences (i) and (iii) on both sides. Therefore, with the other examples as well, the zones corresponding to the zone sequence (ii) of Example 1 each can be grasped as a connection zone having a gentle and non-blaze shape with its inclination angle of the blaze shaped phase profile made smaller than that of the zones belonging to other zone sequences in the same zone group.

Besides, the blaze shaped zones belonging to the other zone sequences (i) and (iii) include a peak point having a plus-side phase peak at the inner radial end of the inclination region as well as a valley bottom point having a minus-side phase peak at the outer radial end thereof. In contrast to this mode, the connection zone is set with a characteristic phase profile for which none of a peak point at the inner radial end and a valley bottom point at the outer radial end is included.

Moreover, in the case of having the phase profile in which the zone groups comprising a plurality of zone sequences are repeated as described above, it is also possible to determine which zone sequence is targeted to be the connection zone by, for example, performing simulation with respect to various types of modes in consideration of the required optical characteristics or the like. It is realistically possible to perform simulation by varying the zone sequence to which the connection zone is set, or by varying the inclination angle of the phase profile of the connection zone and examine the characteristic tendency so as to set the optical characteristics.

Meanwhile, with the present invention profile, it is important that the sign of the inclination of the blaze of the specific zone (adjustment zone) is reversed (including the inclination is 0) with respect to the blaze of the corresponding zone of the standard profile or the blaze of the zone of the other zone sequences. Thus, the specific shape of the inclined portion that is the blaze trajectory is not limited, and for example, in addition to a straight line, a parabolic shape, and furthermore, a shape expressed by a trigonometric function such as a Sine function, or a trajectory of combination of these and the like can also be the target of implementation. Besides, even if the blaze of the standard profile has a curved shape, the blaze having a straight line shape with reversed inclination in the present invention profile may be adopted.

Moreover, in the case in which a connection zone is formed in the blaze of a specific zone sequence, it is not necessary to form the connection zone to all the zone groups belonging to such zone sequence, but is acceptable that only the blaze of such zone sequence existing in a specific zone group serves as the connection zone or the adjustment zone.

From the examples described above, we can see that by adopting the phase profile to which the adjustment zone or the connection zone is set according to the present invention, in the diffractive multi-focal ophthalmic lens, it is possible to adjust the optical characteristics. Besides, we can see that in order to enhance the light energy level at a specific focal point position, the enhancement can also be realized by the light energy level at another focal point position being kept low. Also, according to the preceding examples, with respect to the focal point position aimed at enhancing the light energy level, it is conceivable that reducing the light energy level of the adjacent focal point position is effective. Additionally, it would also be understood that the present invention can preferably be applied in order to reduce the light energy level of the focal point existing at the position sandwiched between the required focal points, thereby making it possible to tune the optical characteristics while avoiding an adverse effect on the focal point at the position adjacent to the focal point for which the light energy level is reduced.

Furthermore, no particular limitation is imposed as to which zone is adopted as the adjustment zone or the connection zone, and this can be selected by performing simulation as described above. However, as one selection criterion, it is conceivable to adopt the zone by excluding the zone with the maximum zone pitch in a single zone group. Specifically, in general, the image-formation characteristics of the focal point image plane of the 0th order diffracted light among the lights made incident on a lens and emitted is described by Fourier transform of the pupil function representing the lens characteristics. For the phase function configuring the pupil function as well, it is also possible to grasp the image-formation characteristics from the Fourier transform analogy. For example, a sawtooth form periodic function can be considered to provide the point spread function including a peak distribution similar to the Fourier transform spectrum for the sawtooth function with respect to the image-formation characteristics of the focal point image plane, and it can also be considered that weak peaks generated at the positions away from the image plane center cause halo or the like. On the other hand, an item for which the inclination of the blaze of a specific zone in the sawtooth form is reversed gives a pseudo triangular shape between adjacent zones, and is similar to the trigonometric function shape as the Fourier spectral component. Thus, the Fourier transform spectrum has a structure mainly comprising a low-frequency spectrum, and provides the point spread function for which the noise peaks do not expand to outer peripheral region. Accordingly, from the analogy of Fourier transform for the sawtooth function, for a blaze of which a zone period is short, in other words, the blaze of the region with a narrow zone pitch, a weak peak noise is likely to be generated up to the outer peripheral part with the point spread function. Thus, it is also conceivable that such zone can be a preferred target zone for being adopted as the adjustment zone or the connection zone.

Also, considering ease of production of the diffractive lens or considering the effect on the basic optical characteristics of the diffractive lens, among a plurality of zone sequences, the zone sequence excluding the zone sequence with the maximum phase amplitude is preferably adopted as the adjustment zone or the connection zone. Incidentally, in the preceding examples, among a plurality of zone sequences, the zone sequence (ii) with the minimum phase amplitude is adopted as the adjustment zone or the connection zone.

Moreover, it would also be acceptable to set the inclination angle of the zone defined by the following equation with an absolute value that is smaller than those of other zones in the adjustment zone or the connection zone. As shown in the preceding examples in particular, the inclination angle is preferably set within the range of 0 to 20 radians/mm$^2$. Specifically, Example 1 adopts the adjustment zone or the connection zone having the inclination angle of 0 radians/mm$^2$, while Example 7 adopts the adjustment zone or the connection zone having the inclination angle of 3.44 radians/mm$^2$.

Inclination angle=(absolute value of phase constant× 2×π)/zone area (unit: radians/mm$^2$)

Besides, it is preferable to set the phase shift of the adjustment zone or the connection zone in the present invention within the range of $-\pi$ to $+\pi$ radians with respect to the reference line of the phase, as described in Examples 1 to 7. For example, the phase shift can be set within the range of $-1$ to $+1$ radians as shown in Examples 1, 4, and 5, and can be set with the reversed inclination that intersects the reference line as shown in Examples 4, 5, and 7. Furthermore, in the case of adopting the mode wherein the phase constant h is 0 as well, it would be acceptable to set the phase profile so as to be aligned with the reference line as described in Example 1, or otherwise, to set the phase profile so as to match the valley bottom point or the peak point that are positioned at the inner radial end or the outer radial end of such zone as described in Examples 2 and 3. Moreover, as shown in Examples 1 to 5, it would also be possible to form the adjustment zone or the connection zone with the zone profile that connects the stepped parts, which are positioned at the inner and outer radial ends and are orthogonal to the reference line, at the mid-positions of the height. However, it would also be acceptable to adopt the zone profile that extends from the valley bottom point or the peak point at one of the inner and outer radial ends as shown in Example 6, or to adopt the zone profile that directly connects the valley bottom point positioned at one of the inner and outer radial ends and the peak point positioned at the other as shown in Example 7.

Whereas Examples 1 to 7 described above are each grasped as including the zone groups comprising three zone sequences, they can also be grasped as an item such that by the zone profile of one zone sequence (ii) having a reversed inclination, such zone is substantially eliminated. From such point of view, the phase profile described in each example can be interpreted as an item such that the zone groups comprising two zone sequences exist repeatedly in the radial direction. When objectively grasping by seeing the phase profile of Example 1 and 4 for example, it can be understood that the zone groups comprising two zone sequences arranged so as to be mutually adjacent in the radial direction are connected to each other by the connection zone having a non-blaze shape.

Incidentally, in Examples 1 to 7, when the zone groups α1, α2, and α3 comprising the zone sequences (i), (ii), and (iii) are grasped, the areas of the regions of the zone groups are equal as shown in Table 16. However, the present invention does not absolutely require that the areas of the zone groups α1, α2, and α3 be equal as described.

TABLE 16

| Zone No. i | Zone radius $r_i$ (mm) | Zone group | Area of zone group (mm²) |
|---|---|---|---|
| 1 | 0.5225 | | |
| 2 | 0.7389 | α1 | 2.57 |
| 3 | 0.9050 | | |
| 4 | 1.0450 | | |
| 5 | 1.1683 | α2 | 2.57 |
| 6 | 1.2798 | | |
| 7 | 1.3824 | | |
| 8 | 1.4778 | α3 | 2.57 |
| 9 | 1.5675 | | |
| 10 | 1.6523 | | |
| 11 | 1.7329 | α4 | 2.57 |
| 12 | 1.8100 | | |
| 13 | 1.8839 | | |

Furthermore, with the preceding examples, the entire surface of the lens substantially constitutes the optical part. However, as with a contact lens, it is also possible to suitably provide a peripheral part that does not impart an optical effect on the eye optical system, etc. in the lens outer peripheral part. Also, in the optical part as well, a diffraction grating can be provided partially only in prescribed regions in the radial direction. For example, it is also possible to provide a refractive lens at the radially inner side of the optical part, while providing a diffraction grating at the radially outer side thereof to obtain a diffractive lens, etc.

It is also possible to apply the present invention to at least a portion of the region of which the diffraction grating is set in the diffractive multi-focal ophthalmic lens. For example, in a diffractive lens for which the diffractive structure is set to the entire area of the optical part, it would also be acceptable to limitedly set the adjustment zone or the connection zone according to the present invention only to the radially inner region, only to the radially outer region, or only to the region of radially middle portion. While in the present examples, the standard profile with the addition power being P=4 D is targeted, such addition power can desirably be modulated. Thus, the adjustment zone or the connection zone similar to those of the preceding examples can be set to the standard profile with the modulated addition power as well, thereby exhibiting similar effect of the invention.

Yet furthermore, the phase function given by the present invention is realized by setting as a diffraction grating in the ophthalmic lens. Here, for the optical material of the ophthalmic lens for realizing the diffraction grating, it is possible to use various materials known from the past according to the desired ophthalmic lens such as contact lens, IOL, ICL, and eyeglass lenses. Also, the diffraction grating that gives the blaze shaped phase function set based on the present invention can be realized by adjusting and setting the light transmission speed in each site of the lens, for example. However, for practical use, it is preferable to realize this diffraction grating by providing a relief structure that reflects the optical path length correlating to the phase in the lens surface, for example. Alternatively, with a laminated structure lens comprising materials of different light transmission speeds (refractive index), it is also possible to set a relief structure for the boundary surface of the materials, thereby making the lens surface be smooth, or be a refracting surface, etc. (see Japanese Unexamined Patent Publication No. JP-A-2001-042112). The relief structure of the lens surface or inner surface can be formed, based on a known manufacturing method of a contact lens, IOL, ICL, etc., through a known technique of implementing chemical or mechanical surface processing such as etching, lathe turning on the optical material, for example.

Figures 2A, 2B, 2C, 2D:
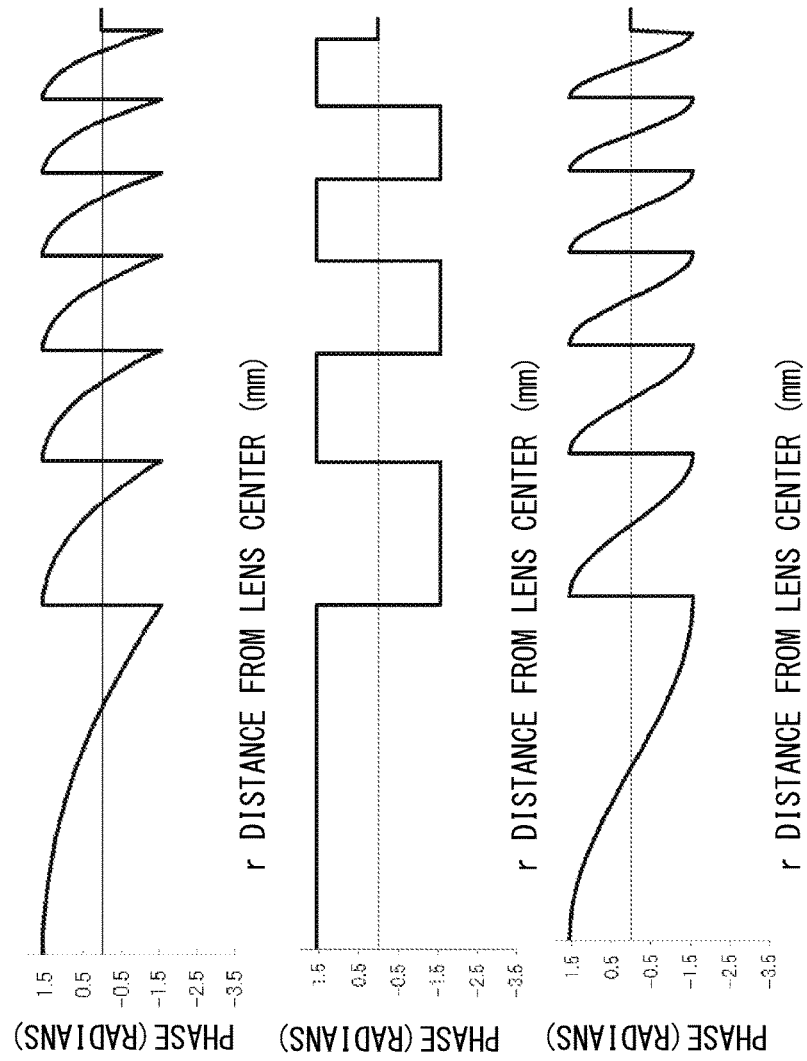
FIGS. 2A-2D are graphs each showing an example of a blaze as a mode of the phase function in the diffractive lens.
Figure 3:
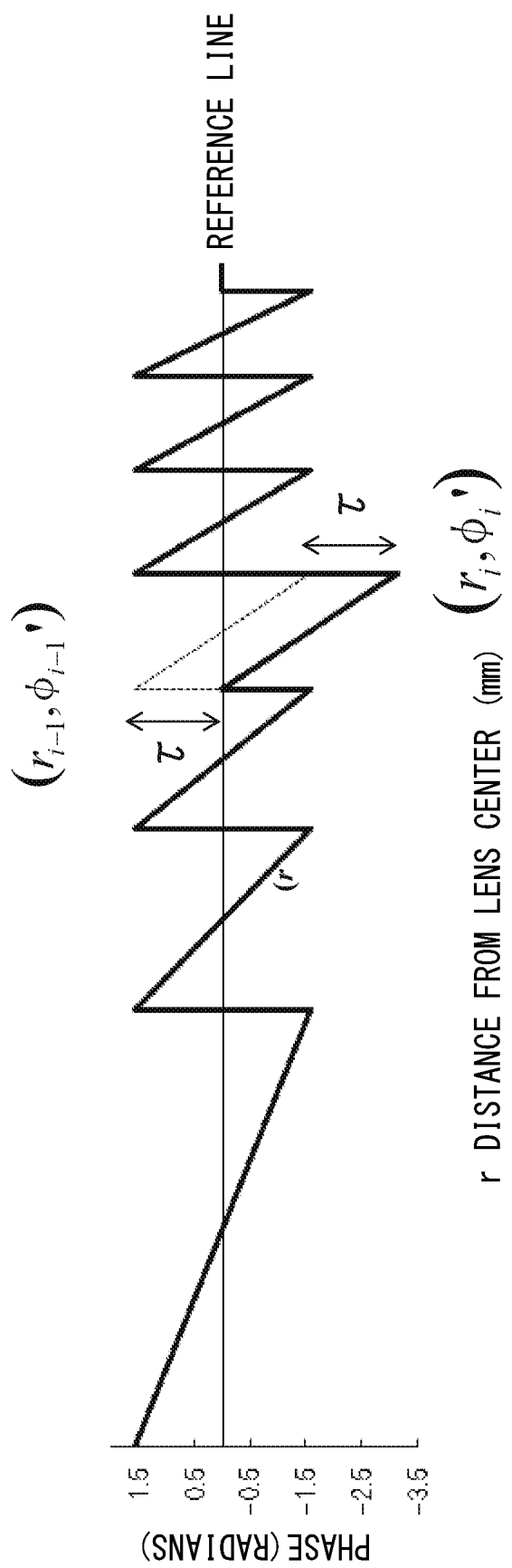
FIG. 3 is a drawing for explaining a mode of the blaze given by the phase shift τ.
Figure 4:
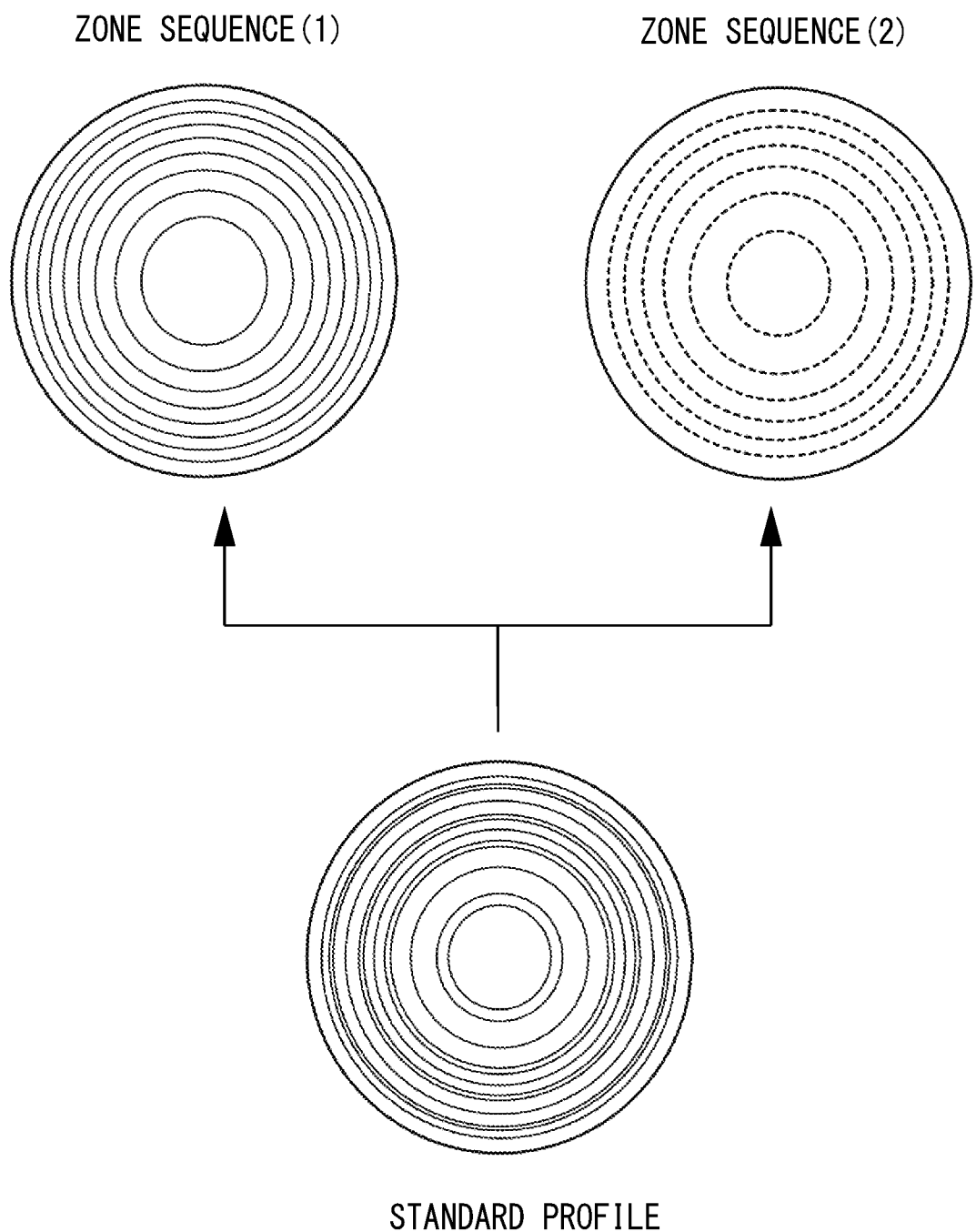
FIG. 4 is a drawing for explaining a structure for which, as one example of a blaze of a diffraction grating, a phase profile of a lens having a standard profile can be grasped as an overlapping of two zone sequences (1) and (2).

Moreover, whereas the adjustment zone or the connection zone according to the present invention can be set, as a specific zone profile, with the modes such as shown in FIG. 2 including a linear function expressed by preceding Equation 6, for example, such specific modes should be recognized as merely design modes. That is, the designed zone profile is provided on the optical surface of the lens by the chemical or mechanical processing technology as described above so as to obtain the ophthalmic diffractive multi-focal lens of structure according to the present invention. However, it should be understood that because of reasons of accuracy during such processing, or because of reasons of measurement accuracy if the obtained optical surface of the lens is measured, it is difficult to specifically grasp the profile of exact design. For example, it is conceivable that clear edges are difficult to be confirmed at the radially both ends of each zone, or that the radially both ends of the adjustment zone or the connection zone in particular are grasped as a mode that has no clear edge and connects to the adjacent zone with a smooth curved shape. Therefore, the actual product should be recognized as including the fact that the theoretical or design zone profile is different from the geometric shape grasped in the actual lens. Besides, even with such a case in which clear edges do not exist at the both ends of the zone profile, the technical effect of the present invention can be exhibited, thereby being included within the technical scope of the present invention.

The ophthalmic lens provided with the diffraction grating imparted with the phase profile according to the present invention is adaptable to any ophthalmic lens regardless of specific types. That is, as long as the environmental condition in which the lens is used is taken into consideration, the contact lens or IOL can be understood without distinguishing each other. Besides, an ICL and eyeglass lenses can also be grasped as the examples of the present invention. Specifically, as the ophthalmic lens to which the present invention is applied, any of a contact lens, eyeglasses, an intraocular lens, etc., can be a specific subject, and also a cornea insertion lens for correcting visual power implanted intrastromally in the cornea, or an artificial cornea, etc. can be the subject. Besides, for contact lenses, it is possible to suitably apply the present invention to a hard, oxygen-permeable hard contact lens, a hydrogel or non-hydrogel soft contact lens, and also an oxygen-permeable hydrogel or non-hydrogel soft contact lens containing a silicone component, etc. Also, for intraocular lenses, it is possible to suitably apply the present invention to any intraocular lens, such as a hard intraocular lens, a soft intraocular lens that can be folded and inserted intraocularly.

Here, the present inventor performed simulations in which the present invention is applied to a contact lens and an intraocular lens, in addition to the eyeglasses, and confirmed that the present invention was adaptable thereto. According to the simulations, it was possible to obtain effects similar to those of the embodiments described above. It was also confirmed that, for example, when the present invention was applied to a contact lens or an intraocular lens, by suppressing the light energy level on a specific optical axis, an effect of suppressing halo and blurred vision was achieved. If needed, such confirmation tests are easy for those skilled in the art to repeat under the conditions noted hereafter.

Evaluation of Halo or the Like

Evaluation of halo or the like can be performed by simulation of the point spread function. As a specific example, it can be evaluated by the diffraction profile of the present invention being provided as a relief structure on the front surface of each lens noted hereafter, the lens being inserted into the eye of a person, or a worn state being constructed by simulation, and the point spread function being calculated to check the image formed on the retina in that eye optical system. In simulation, it is possible to use VirtualLab (product name) made by LightTrans GmbH. Considering the optical system of the human eye, it is desirable that the incident light set to the simulation of the point spread function be such that, the same as with simulation of intensity distribution on the optical axis, the wavelength is 546 nm, and the light source is a point light source at an infinite distance.

Simulation as an Intraocular Lens

It is possible to perform simulation with respect to an implementation mode in an intraocular lens by arranging the eye optical system in sequence of the cornea, aqueous humor, iris, intraocular lens, vitreous body, and retina, and determining the refractive index and shape based on human eye data. Specifically, it is preferable to determine the refractive power of the intraocular lens and the pupil diameter as noted below.

Intraocular lens 0th order diffracted light refractive power (diopter): around 20 D Pupil diameter: around 3 to 5 mm in diameter Simulation as a Contact Lens It is possible to perform simulation with respect to an implementation mode in a contact lens by arranging the eye optical system in sequence of the contact lens, cornea, aqueous humor, iris, crystalline lens, vitreous body, and retina, and determining the refractive index and shape based on human eye data. Specifically, it is preferable to determine the refractive power of the contact lens and the pupil diameter as noted below.

Contact lens 0th order diffracted light refractive power (diopter): around 0 D

Pupil diameter: around 3 to 5 mm in diameter

The present invention is adaptable to an ophthalmic diffractive multi-focal lens giving three or more focal points. However, as will also be apparent from the preceding fifteenth mode of the present invention, it is also acceptable to provide the present invention as an ophthalmic diffractive multi-focal lens including optical characteristics such that, for example, the light energy level of one focal point among three focal points generated in the optical axis direction is reduced so that substantially two focal points are set.

In addition, though not listed as individual examples, the present invention can be implemented in modes for which various changes, modifications, and improvements, etc. are made based on the knowledge of those skilled in the art, and it goes without saying that such an implementation mode is included in the scope of the present invention as long as it does not stray from the spirit of the present invention.

The invention claimed is:

1. An ophthalmic diffractive multi-focal lens comprising
    a diffractive structure including a phase profile having a plurality of blaze shaped zones being set in a concentric circle form, the diffractive structure generating at least three focal points in an optical axis direction, wherein
    at least one of the zones serves as an adjustment zone for which an inclination direction in the phase profile is reversed with respect to that of other zones,
    a light intensity level giving a peak at a position away from the three focal points in a light intensity distribution of transmitted light in the optical axis direction is kept low in comparison with a phase profile without the adjustment zone, and
    an inclination angle of the adjustment zone in the phase profile specified by a following equation is not greater than 20 radians/mm$^2$:

inclination angle=(absolute value of phase constant× 2×π)/zone area (unit: radians/mm$^2$).

2. The ophthalmic diffractive multi-focal lens according to claim 1, wherein in the phase profile, a phase shift of the adjustment zone is set within a range of $-\pi$ to $+\pi$ radians with respect to a reference line of a phase (an r axis of $\phi=0$ in an r–$\phi$ coordinate system of a phase function $\phi(r)$) in the phase profile.

3. The ophthalmic diffractive multi-focal lens according to claim 1, wherein in the phase profile, the adjustment zone is set such that the adjustment zone intersects a reference line of a phase (an r axis of $\phi=0$ in an r–$\phi$ coordinate system of a phase function $\phi(r)$) in the phase profile.

4. An ophthalmic diffractive multi-focal lens comprising
    a diffractive structure including a phase profile having a plurality of blaze shaped zones being set in a concentric circle form, the diffractive structure generating at least three focal points in an optical axis direction, wherein
    at least one of the zones serves as an adjustment zone for which an inclination direction in the phase profile is reversed with respect to that of other zones,
    a light intensity level giving a peak at a position away from the three focal points in a light intensity distribution of transmitted light in the optical axis direction is kept low in comparison with a phase profile without the adjustment zone, and,
    the peak in the light intensity distribution of the transmitted light in the optical axis direction that is kept low in comparison with the phase profile without the adjustment zone is a peak that exists within a range of ±5 diopters with respect to a focal point position of at least one of the three focal points in optical characteristics given by the phase profile without the adjustment zone, and is a peak that has a peak level which is not less than one-third of that of at least one of the three focal points.

5. An ophthalmic diffractive multi-focal lens comprising
    a diffractive structure including a phase profile having a plurality of blaze shaped zones being set in a concentric circle form, the diffractive structure generating at least three focal points in an optical axis direction, wherein
    at least one of the zones serves as an adjustment zone for which an inclination direction in the phase profile is reversed with respect to that of other zones,
    a light intensity level giving a peak at a position away from the three focal points in a light intensity distribution of transmitted light in the optical axis direction is kept low in comparison with a phase profile without the adjustment zone, and,
    a peak level of the peak in the light intensity distribution of the transmitted light in the optical axis direction that is kept low in comparison with the phase profile without the adjustment zone is not greater than 50% of all peak levels of the three focal points.

6. The ophthalmic diffractive multi-focal lens according to claim 1, wherein the phase profile has a periodic structure of zone groups repeated in a radial direction, the zone groups comprising a certain number of the zones, and the zones that correspond in at least two of the zone groups each serve as the adjustment zone.

7. The ophthalmic diffractive multi-focal lens according to claim 1, wherein the phase profile set in the concentric circle form is set based on a Fresnel pitch.

8. An ophthalmic diffractive multi-focal lens comprising a diffractive structure including a phase profile having a plurality of blaze shaped zones being set in a concentric circle form, the diffractive structure generating at least three focal points in an optical axis direction, wherein at least one of the zones serves as an adjustment zone for which an inclination direction in the phase profile is reversed with respect to that of other zones, a light intensity level giving a peak at a position away from the three focal points in a light intensity distribution of transmitted light in the optical axis direction is kept low in comparison with a phase profile without the adjustment zone, and the phase profile to which the plurality of blaze shaped zones generating at least three focal points in the optical axis direction are set in the concentric circle form using the diffractive structure serves as an adjusted profile, the adjusted profile being dividable into starting profiles that are a plurality of phase profiles configured to be overlapped each other, and the adjusted profile being a composite profile generated by the phase profiles being overlapped, and at least one of the zones of the composite profile serves as the adjustment zone for which an inclination direction has a different blaze shape from an overlapping of the starting profiles.

9. The ophthalmic diffractive multi-focal lens according to claim 1, wherein the blaze shaped phase profile is expressed by Equation 1:

$$\phi(r) = \frac{\phi_i - \phi_{i-1}}{r_i - r_{i-1}} \times r + \frac{\phi_{i-1} \times r_i - \phi \times r_{i-1}}{r_i - r_{i-1}} + \tau \quad \text{[Equation 1]}$$

r: Radial distance from the lens center
$r_{i-1}$: Inner diameter (radius) of the ith zone
$r_i$: Outer diameter (radius) of the ith zone
$\phi_{i-1}$: Phase at the inner diameter (radius) position of the ith zone
$\phi_i$: Phase at the outer diameter (radius) position of the ith zone
τ: Phase shift.

10. The ophthalmic diffractive multi-focal lens according to claim 1, wherein a reduction ratio in a light intensity level due to the adjustment zone for a light intensity peak that is fourth highest in the light intensity level after the three focal points is greater than reduction ratios in light intensity levels due to the adjustment zone for light intensity peaks of the three focal points.

11. A method for manufacturing an ophthalmic diffractive multi-focal lens capable of generating at least three focal points in an optical axis direction using a diffractive structure comprising a plurality of zones in a concentric circle form, the method comprising:

setting a phase profile including the zones having a blaze shape inclining in a same direction, the phase profile generating the at least three focal points; and reducing a light intensity level giving a peak at a position away from the three focal points in a light intensity distribution of transmitted light in the optical axis direction by setting an adjustment zone for which an inclination direction of at least one of the zones of the phase profile is reversed with respect to that of other zones, wherein an inclination angle of the adjustment zone in the phase profile specified by a following equation is not greater than 20 radians/mm$^2$:

inclination angle=(absolute value of phase constant× 2×π)/zone area (unit: radians/mm$^2$).

* * * * *